United States Patent
Walsh et al.

(10) Patent No.: US 9,128,058 B2
(45) Date of Patent: *Sep. 8, 2015

(54) METHOD FOR SEPARATION AND CHARACTERIZATION OF MICROORGANISMS USING IDENTIFIER AGENTS

(75) Inventors: John Walsh, Durham, NC (US); Jones M. Hyman, Wake Forest, NC (US); Thurman Thorpe, Durham, NC (US); Bradford Clay, Wildwood, MO (US)

(73) Assignee: bioMerieux, Inc., Durham, NC (US)

( * ) Notice: Subject to any disclaimer, the term of this patent is extended or adjusted under 35 U.S.C. 154(b) by 1047 days.

This patent is subject to a terminal disclaimer.

(21) Appl. No.: 12/589,985

(22) Filed: Oct. 30, 2009

(65) Prior Publication Data

US 2010/0129814 A1 May 27, 2010

Related U.S. Application Data

(60) Provisional application No. 61/110,187, filed on Oct. 31, 2008.

(51) Int. Cl.
- *C12Q 1/04* (2006.01)
- *G01N 21/65* (2006.01)
- *G01N 33/68* (2006.01)
- *G01N 21/35* (2014.01)
- *G01N 21/3581* (2014.01)

(Continued)

(52) U.S. Cl.
CPC ..... *G01N 21/65* (2013.01); *C12Q 1/04* (2013.01); *G01N 33/6848* (2013.01); *G01N 21/35* (2013.01); *G01N 21/3581* (2013.01); *G01N 21/47* (2013.01); *G01N 21/64* (2013.01)

(58) Field of Classification Search
None
See application file for complete search history.

(56) References Cited

U.S. PATENT DOCUMENTS

| 3,928,139 A | 12/1975 | Dorn |
| 3,932,222 A | 1/1976 | Dorn |
| 4,038,150 A | 7/1977 | Dorn et al. |

(Continued)

FOREIGN PATENT DOCUMENTS

| DE | 19801661 A1 | 7/1999 |
| EP | 107070 A1 * | 5/1984 |

(Continued)

OTHER PUBLICATIONS

Fluorinert FC-40 Product Information. Mar. 2010.*

(Continued)

*Primary Examiner* — Samuel Woolwine

(57) ABSTRACT

The present invention is directed to a method for separating, characterizing and/or identifying microorganisms in a test sample. The method of the invention comprises an optional lysis step for lysing non-microorganism cells that may be present in a test sample, followed by a subsequent separation step. The method may be useful for the separation, characterization and/or identification of microorganisms from complex samples such as blood-containing culture media. The invention further provides for the use of one or more identifier agents and interrogating the microorganism sample and/or said one or more identifier agents to produce measurements which characterizing and/or identifying the microorganism based on the produced measurements and/or the presence or absence of the identifier agent or a metabolized form of the identifier agent in the microorganism sample.

15 Claims, 5 Drawing Sheets

Post-centrifugation of lysed S. aureus-containing blood culture broth

(51) Int. Cl.
  G01N 21/47 (2006.01)
  G01N 21/64 (2006.01)

(56) References Cited

U.S. PATENT DOCUMENTS

| | | | |
|---|---|---|---|
| 4,131,512 A | 12/1978 | Dorn | |
| 4,212,948 A | 7/1980 | Dorn | |
| 4,410,630 A | 10/1983 | Zierdt | |
| 4,693,972 A * | 9/1987 | Mansour et al. | 435/34 |
| 4,829,005 A | 5/1989 | Friedman et al. | |
| 4,847,198 A | 7/1989 | Nelson et al. | |
| 5,474,910 A | 12/1995 | Alfano | |
| 5,938,617 A | 8/1999 | Vo-Dinh | |
| 5,948,610 A | 9/1999 | Ho et al. | |
| 6,121,055 A * | 9/2000 | Hargreaves | 436/526 |
| 6,177,266 B1 | 1/2001 | Krishnamurthy et al. | |
| 6,346,421 B1 | 2/2002 | Anderson et al. | |
| 6,780,602 B2 | 8/2004 | Powers et al. | |
| 6,834,237 B2 | 12/2004 | Noergaard et al. | |
| 6,875,616 B1 | 4/2005 | Forssmann et al. | |
| 7,020,559 B1 | 3/2006 | Demirev et al. | |
| 7,070,739 B1 | 7/2006 | Anderson et al. | |
| 2002/0086289 A1 | 7/2002 | Straus | |
| 2004/0185437 A1 | 9/2004 | Hermet et al. | |
| 2004/0197771 A1 | 10/2004 | Powers et al. | |
| 2005/0147621 A1 * | 7/2005 | Higgins et al. | 424/200.1 |
| 2005/0273267 A1 | 12/2005 | Maione et al. | |
| 2007/0037135 A1 | 2/2007 | Barnes et al. | |
| 2007/0175278 A1 | 8/2007 | Puppels et al. | |
| 2007/0254320 A1 * | 11/2007 | Olstein | 435/7.32 |
| 2007/0269897 A1 | 11/2007 | Tanaka et al. | |
| 2008/0009029 A1 | 1/2008 | Govorun et al. | |
| 2008/0050829 A1 | 2/2008 | Ivey et al. | |
| 2008/0297789 A1 | 12/2008 | Stewart et al. | |
| 2009/0156943 A1 | 6/2009 | Phillips et al. | |

FOREIGN PATENT DOCUMENTS

| | | |
|---|---|---|
| WO | WO0221108 | 3/2002 |
| WO | WO2004014322 | 2/2004 |
| WO | WO2005068647 | 7/2005 |
| WO | WO 2006091630 A2 * | 8/2006 |
| WO | WO2007030020 | 3/2007 |
| WO | WO2009011585 | 1/2009 |
| WO | WO2009049171 | 4/2009 |
| WO | WO2009065580 | 5/2009 |
| WO | WO2009100197 | 8/2009 |
| WO | WO2009105061 | 8/2009 |

OTHER PUBLICATIONS

Manafi et al. Fluorogenic and chromogenic substrates used in bacterial diagnostics. Microbiol Rev 55(3):335-348.*
Dorn et al. New Centrifugation Blood Culture Device. Journal of Clinical Microbiology 7(1):52-54 (1978).*
Mansour et al. Detection of *Escherichia coli* in Blood Using Flow Cytometry. Cytometry 6:186-190 (1985).*
Estes et al.; Reagentless Detection of Microorganisms by Intrinsic Fluorescence; Biosens Bioelectron. (2003) vol. 18 No. 5-6 511-519.
Mason et al.; Taxonomic Identification of Microorganisms by Capture and Intrinsic Fluorescence Detection; Biosens Bioelectron. (2003) vol. 18, No. 5-6, pp. 521-527.
Rativa et al.; Optical Spectroscopy on in vitro Fungal Diagnosos; Conf Proc IEEE Eng Med Biol Soc. (2008) vol. 1, pp. 4871-4874.
Ackermann et al., Rapid Analysis of Antibiotic-Containing Mixtures from Fermentation Broths by Using Liquid Chromotography—Electrospray Ionization—Mass Spectrometry and Matrix-Assisted Laser Desorption Ionization—Time-of-Flight—Mass Spectrometry; J. Amer. Soc. Mass Spec. (Dec. 1, 1996) vol. 7 No. 12 pp. 1227-1237.
Alimova et al.;Native Fluorescence Changes Induced by Bactericidal Agents;IEEE Sensors Journal (2005)vol. 5 No. 4 pp. 704-711.
Ammor MS; Recent Advances in the use of Intrinsic Fluorescence for Bacterial Identification and Characterization;J. Fluoresc (2007) vol. 17 pp. 455-459.
Bernhardt et al.; Detection of Bacteria in Blood by Centrifugation and Filtration; J. Clin. Micro. (1991) vol. 29 No. 3 pp. 422-425.
Bhatta et al.; Use of Fluorescence Spectroscopy to Differentiate Yeast and Bacterial Cells; Appl Microbiol Biotechnol (2006) vol. 71 pp. 121-126.
Bronk et al.; Variability of Steady State Bacterial Fluorescence with Respect to Growth Conditions; App. Spectroscopy (1993) vol. 47 No. 4 pp. 436-440.
Dalterio et al.; The Steady-State and Decay Characteristics of Primary Fluorescence From Live Bacteria; App. Spectroscopy (1987) vol. 41 No. 2 pp. 234-241.
Dorn et al.; Blood Culture Technique Based on Centrifugation: Developmental Phase; J. Clin. Micro. (Mar. 1976) vol. 3 No. 3 pp. 251-257.
Abstract of Estes et al.; Reagentless Detection of Microorganisms by Intrinsic Fluorescence; Biosens Bioelectron. (2003) vol. 18 No. 5-6, pp. 511-519.
Fenselau et al.; Characterization of intact microorganisms by MALDI Mass Spectrometry; Mass Spectrometry Reviews (2001) vol. 20 No. 4 pp. 157-171.
Fukushima et al.; Rapid Separation and Concentration of Food-Borne Pathogens in Food Samples Prior to Quantification by Viable-Cell Counting and Real-Time PCR; App. Envir. Micro. (Jan. 2007) vol. 73 (1) pp. 92-100.
Giana et al.; Rapid Identification of Bacterial Species by Fluorescence Spectroscopy and Classification Through Principal Components Analysis; J. Fluoresc (2003) vol. 13 pp. 489-493.
Gill et al. ; Comparison of Lysis-Centrifugation with Lysis-Filtration and a Conventional Unvented Bottle for Blood Culture; J. Clin. Micro. (1984) vol. 20. No. 5 pp. 927-932.
Ginell et al. ; Fluorescent Spectrophotometry in the Identification of Bacteria; J. Appl. Bact. (1972) 35(1) pp. 29-36.
Huffman et al.; New method for the detection of micro-organisms in blood: application of quantitative interpretation model to aerobic blood cultures; J. Biom. Optics (May/Jun. 2009) 14(3) pp. 034043-1 through 034043-10.
Jarvis Roger et al.; Surface enhanced Raman Scattering for the Rapid Discrimination of Bacteria; Faraday Discussions Royal Society of Chemistry (Jan. 1, 2006) vol. 132 pp. 281-292.
Kruger et al.; Analysis of the substrate specificity of the *Staphylococcus aureus* sortase transpeptidase SrtA; Biochemistry (Feb. 1, 2004) vol. 43 No. 6 pp. 1541-1551 (Feb. 1, 2004).
Leblanc et al.; Monitoring the identity of bacteria using their intrinsic fluorescence; FEMS Microbiology Letters (2002) 211 pp. 147-153.
Lefmann et al.; Novel Mass Spectometry-Based Tool for Genotypic Identification of Mycobacteria ; J. Clin. Micro. (2004) vol. 42 No. 1 pp. 339-346.
Maquelin et al.; Identification of Medically Relevant Microorganisms by Vibrational Spectroscopy; J. Micro. Methods, (Nov. 1, 2002) vol. 51, No. 3, pp. 255-271.
Maquelin et al.; Prospective Study of the Performance of Vibrational Spectroscopies for Rapid Identification of Bacterial and Fungal Pathogens Recovered from Blood Cultures; J. Clin. Micro., (Jan. 1, 2003) vol. 41, No. 1, pp. 324-329.
Abstract of Mason et al.; Taxonomic Identification of Microorganisms by Capture and Intrinsic Fluorescence Detection; Biosens Bioelectron. (2003) vol. 18, No. 5-6, pp. 521-527.
Mothershed et al.; Nucleic acid-based methods for the detection of bacterial pathogens: Present and future considerations for the clinical laboratory; Clinica Chimica Acta, (Jan. 1, 2006) vol. 363, No. 1-2, pp. 206-220.
Neugebauer et al.; Characterization of Bacterial Grwoth and the Influence of UV Resonance Raman Spectroscopy; Biopolymers, (Jul. 2006) vol. 82, No. 4, pp. 306-311.
Pau et al.; A Rapid Enzymatic Procedure for "Fingerprinting" Bacteria by Using Pattern Recognition of Two-Dimensional Fluorescence Data; Clin. Chem. (1986) 32/6, pp. 987-991.
Pau et al.; Evaluation of a Forier-Transform-Based Pattern-Recognition Algorithm for Two-Dimensional Fluorescence Data; App. Spectroscopy (1987) vol. 41, No. 3, pp. 496-502.
Popp et al.; Raman-Spectroscopy for a rapid identification of single microorganisms; Proceedings of the Spie—The International Society for Optical Engineering, (2005) vol. 6180, pp. 618024-1.

(56) References Cited

OTHER PUBLICATIONS

Abstract of Rativa et al.; Optical Spectroscopy on in vitro Fungal Diagnosos; Conf Proc IEEE Eng Med Biol Soc. (2008) vol. 1, pp. 4871-4874.
Rosch et al.; Fast and reliable identification of microorganisms by means of Raman spectroscopy; Proceedings of the Spie—The International Society for Optical Engineering, (2007) vol. 6622, pp. 66331A-1.
Rubin et al.; Comparison of the Du Pont Isolator 1.5 Microbial Tube and Trypticase Soy Broth for the Recovery of *Haemophilus influenzae* Type b in Experimental Bacteremia; J. Clin. Micro., (Nov. 1985) vol. 22, No. 5, pp. 815-818.
Sage et al.; Rapid Visual Detection of Microorganisms in Blood Culture; J. Clin. Micro., (Jul. 1984) vol. 20. No. 1, pp. 5-8.
Serebrennikova et al.; Quantitative interpretations of Visible-NIR reflectance spectra of blood; Optics. Society., (Oct. 27, 2008) vol. 16, No. 22, pp. 18215-18229.
Shelly et al.; Characterization of Bacteria by Mixed-Dye Fluorimetry; Clin. Chem. (1983) 29/2, pp. 290-296.
Shelly et al.; Identification of Fluorescent Pseudomonas Species; Clin. Chem. (1980) 26/8, pp. 1127-1132.
Sohn et al.; Fluorescence Spectroscopy for Rapid Detection and Characterization of Bacterial Pathogens; App. Spectroscopy (2009) vol. 63, No. 11, pp. 1251-1255.
Sorrell et al.; Bacterial Identification of Otitis Media With Fluorescence Spectroscopy; Lasers in Surgery and Medicine, (1994) vol. 14, pp. 155-163.
Spector et al.; Noninvasive Fluorescent Identification of Bacteria Causing Acute Otitis Media in a Chinchilla Model; Laryngoscope, (2000) vol. 110, pp. 1119-1123.
Warner et al.; Multicomponent Analysis in Clinical Chemistry by Use of Rapid Scanning Fluorescence Spectroscopy; Clin. Chem. (1976) 22/9, pp. 1483-1492.
Zierdt et al.; Development of a Lysis-Filtration Blood Culture Technique; J. Clin. Microbiology, (Jan. 1977) vol. 5, No. 1, pp. 46-50.
International Search Report and Written Opinion of the International Searching Authority for PCT/US2009/005884 dated Feb. 15, 2010.
Co-pending U.S. Appl. No. 12/589,929 "Methods for the Isolation and Identification of Microorganisms" filed Oct. 30, 2009.
Co-pending U.S. Appl. No. 12/589,936 "Methods for Separation Characterization and/or Identification of Microorganisms using Mass Spectrometry" filed Oct. 30, 2009.
Co-pending U.S. Appl. No. 12/589,952 "Methods for Separation Characterization and/or Identification of Microorganisms using Spectroscopy" filed Oct. 30, 2009.
Co-pending U.S. Appl. No. 12/589,968 "Methods for Separation Characterization and/or Identification of Microorganisms in a Sealed Container" filed Oct. 30, 2009.
Co-pending U.S. Appl. No. 12/589,976 "Methods for Separation Characterization and/or Identification of Microorganisms using Raman Spectroscopy" filed Oct. 30, 2009.
Fazi, S. et al., Bacterial Communities Associated with Benthic Organic Matter in Headwater Stream Microhabitats, Environmental Microbiology (2005) 7(10),1633-1640.
English-language translation of DE 19801661 A1, published Jul. 22, 1999.

* cited by examiner 0.4 OD Suspension of S. aureus ATCC 12600 from SA Bottle

Post-centrifugation of lysed S. aureus-containing blood culture broth

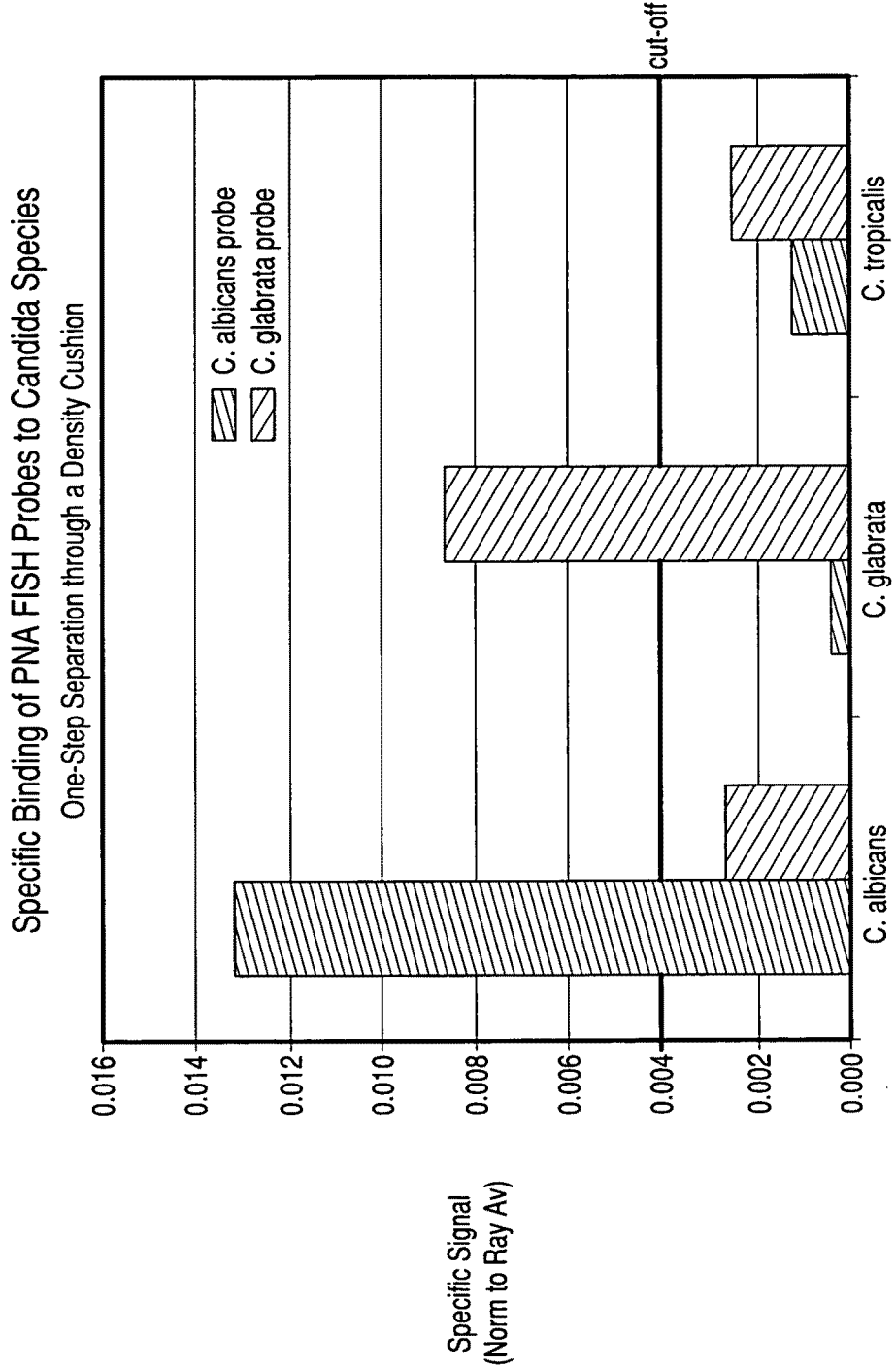

METHOD FOR SEPARATION AND CHARACTERIZATION OF MICROORGANISMS USING IDENTIFIER AGENTS

CROSS REFERENCE TO RELATED APPLICATION

This application claims the benefit of U.S. Provisional Patent Application No. 61/110,187, entitled, "Method and System for Detection and/or Characterization of a Biological Particle in a Sample", filed Oct. 31, 2008, which is incorporated herein.

FIELD OF THE INVENTION

The present invention relates to methods and systems for detecting, isolating and/or identifying microorganisms in a sample. Moreover, the present invention is directed to a method for the enhanced characterization and/or identification of microorganisms using identifier agents.

BACKGROUND OF THE INVENTION

The detection of pathogenic microorganisms in biological fluids should be performed in the shortest possible time, in particular in the case of septicemia for which the mortality remains high in spite of the broad range of antibiotics which are available to doctors. The presence of biologically active agents such as a microorganism in a patient's body fluid, especially blood, is generally determined using blood culture bottles. Bloodstream infections are associated with high morbidity and mortality, yet current diagnostic methods, of culture followed by biochemical identification and antibiotic susceptibility testing, can take several days to perform. Typically, empiric therapy is initiated based on clinical symptoms, and test results only impact clinical decisions when the initial therapy fails. The ability to characterize bloodstream infections within the first few hours, preferably within an hour, after a positive blood culture result would significantly boost the clinical relevance of the diagnostic information provided. Molecular amplification methods have been proposed to fill this need, but serious challenges to this approach remain. The positive blood culture broth itself represents a naturally amplified population of microorganisms with potential for use in a variety of rapid, identification (ID) tests.

Traditional automated phenotypic ID tests, such as the Vitek®, Phoenix™ and Microscan® systems, or manual phenotypic tests such as API require that microorganisms be in an appropriate growth phase and free of interfering media and blood products in order to provide robust results. These systems use colonies grown from the positive broth for 18-24 hours on plated media. However, in an effort to obtain faster results, some laboratories have reported using these systems with microorganisms isolated from positive blood culture bottles. These direct-from-the-bottle tests are not appropriate for all microorganisms (e.g., Gram-positive cocci), are not validated by the test manufacturers, and generally take 3-8 hours to provide results. Faster and more broadly specific tests are urgently needed in order to provide the physician with clinically relevant results within the first few hours, preferably within an hour, after a positive culture result.

Optical spectroscopy methods, such as intrinsic fluorescence (IF), infrared spectroscopy (FTIR), or Raman spectroscopy, and mass spectrometry methods such as MALDI-TOF, have the potential to allow for identification of microorganisms very quickly, but may encounter interference from the many highly fluorescent and absorptive compounds present in liquid microbiological culture media and in clinical samples such as blood or combinations thereof. The most commonly employed methods for recovering microorganisms directly from positive blood culture broth are two-step differential centrifugation and centrifugation in a serum separator tube.

Other methods for separation, characterization and/or identification of microorganisms have been described, include:

U.S. Pat. No. 4,847,198 discloses a method for the identification of microorganisms using UV excited Raman spectroscopy. According to the '198 patent, a bacterial suspension is contacted by a single wavelength in the ultra-violet range. A portion of the light energy used is absorbed and a portion of the light energy is emitted. The emitted light energy, resonance enhanced Raman scattering, is measured as backscattered energy. The energy is processed to produce spectra which are characteristic of the bacteria.

U.S. Pat. No. 5,938,617 to Vo-Dinh is directed to a system which identifies biological pathogens in a sample by exciting a sample with light at several wavelengths and synchronously sampling the emission intensities. The system includes mechanisms for exposing the sample to excitation radiation and thereby generating an emission radiation. The biological pathogens may be viruses and bacteria.

U.S. Pat. No. 6,177,266 discloses a method for the chemotaxonomic classification of bacteria with genus, species and strain specific biomarkers generated by matrix assisted laser desorption ionization time-of-flight mass spectrometry (MALDI-TOF-MS) analysis of either cellular protein extracts or whole cells.

In U.S. Pat. No. 7,070,739 a method is presented to extract, separate, and purify microbes including viruses by two-dimensional ultra-centrifuging directly from body fluids or homogenized tissue. In a first centrifuging step, all particles are removed having a sedimentation speed higher than those of the microbes to be identified. In the second ultra-centrifuging step, isopycnic banding is used in liquids filled in to form a wide-range density gradient, using special serrated centrifuge tubes. According to the patent, the separation technique can be used for detecting banded particles by light scatter or fluorescence using nucleic acid specific dyes, and for recovering the banded particles in very small volumes for characterization by mass spectrometry of viral protein subunits and intact viral particles, and by fluorescence flow cytometric determination of both nucleic acid mass and the masses of fragments produced by restriction enzymes.

U.S. Pat. Appl. Pub. No. 2007/0037135 discloses a system for the identification and quantification of a biological sample suspended in a liquid. The system includes a fluorescence excitation module with at least one excitation light source; a sample interface module optically coupled to the fluorescence excitation module for positioning a biological sample to receive excitation light from the at least one excitation light source; a fluorescence emission module optically coupled to the sample interface module and comprising at least one detection device for detecting fluorescence excitation-emission matrices of the biological sample; and a computer module operatively coupled to the fluorescence emission module. The computer module performs multivariate analysis on the fluorescence excitation-emission matrices of the biological sample to identify and quantify the biological sample. However, the '135 application does not discuss identification and quantification of microorganisms from complex biological samples, such as blood.

U.S. Pat. Appl. Pub. No. 2007/0175278 describes using a liquid culture medium for culturing a sample of interest, including for example, blood, urine, feces, intravenous catheters etc., industrial production lines, water systems, a food product, a cosmetic product, a pharmaceutical product and a forensic sample. Subsequently, the microorganisms can be harvested from the liquid medium by methods known in the art, e.g. by centrifugation. The concentrated microorganisms may then be transferred to carrier material, optionally after drying, for obtaining a vibrational spectrum. The patent application discusses various methods for identifying and classifying microorganisms, including vibrational spectroscopy, such as Raman spectroscopy.

However, these methods have several drawbacks when attempting to separate and characterize microorganisms from complex samples such as blood-containing culture media. The resultant microbial preparations often contain contaminating red blood cells, platelets, lipid particles, plasma enzymes and cellular debris, which can cause poor results. These methods are also very labor-intensive and unsafe due to steps which can result in aerosol exposure of potentially dangerous pathogens to the user. Simple, safe and reliable methods are needed to isolate microorganisms from clinical samples (e.g., blood culture broth) and other complex samples that are free of these interfering materials and compatible with rapid identification technologies.

SUMMARY OF THE INVENTION

The present invention provides methods for isolating, characterizing and/or identifying microorganisms in a sample. The methods allow for the characterization and/or identification of microorganisms more quickly than prior techniques, resulting in faster diagnoses (e.g., in a subject having or suspected of having septicemia) and identification of contaminated materials (e.g., foodstuffs and pharmaceuticals). The steps involved in the methods of the invention, from obtaining a sample to characterization and/or identification of microorganisms, can be carried out in a very short time frame to produce clinically relevant actionable information, e.g., in less than about 120 minutes. Additionally, the methods of the invention can be fully automated, thereby reducing the risk of handling infectious materials and/or contaminating samples.

In one aspect, the present invention is directed to a method of characterizing and/or identifying a microorganism, comprising:
(a) obtaining a test sample known to contain or that may contain microorganisms;
(b) layering the test sample over a density cushion in a container;
(c) adding an identifier agent to said test sample and/or said density cushion;
(d) centrifuging said container to separate microorganisms from other components of said test sample and forming a pellet of microorganisms;
(e) interrogating said pellet and/or said one or more identifier agents to produce measurements which identify the microorganisms; and
(f) characterizing and/or identifying the microorganisms in the pellet based on the produced measurements and/or the presence or absence of said identifier agent or a metabolized form of the identifier agent in the pellet.

In another aspect, the present invention is directed to a method of isolating and identifying a microorganism, comprising:
(a) obtaining a test sample known to contain or that may contain microorganisms;
(b) optionally lysing cells in said test sample to produce a lysed sample;
(c) separating microorganisms from other components of said lysed sample to form a pellet of microorganisms;
(d) interrogating the pellet to produce measurements which identify the microorganisms;
(e) identifying the microorganisms based on the produced measurements; and
(f) recovering at least a portion of the pellet to produce recovered microorganisms;
(g) conducting one or more further tests on said recovered microorganisms.

In one embodiment, the separation is carried out by layering the sample over a density cushion in a container and centrifuging the container to pellet the microorganisms while the sample medium remains on top of the density cushion. In another embodiment, the container has an optical window at the bottom and/or sides so that the microorganism pellet can be interrogated spectroscopically. The microorganisms can be identified by comparing the spectrum of the pellet to a spectrum or spectra of known microorganisms. The ability to identify microorganisms directly in the pellet without further handling enhances the safety of microbial identification.

In one embodiment, the spectroscopic interrogation is based on intrinsic characteristics of the microorganisms (e.g., intrinsic fluorescence). In other embodiments, the spectroscopic interrogation is based in part on signals obtained from additional agents that are added during the methods of the invention and interact with specific microorganisms or groups of microorganisms.

In another embodiment, the methods further comprise a step of recovering the microorganism pellet, resuspending the microorganism and performing further identification or characterization tests (e.g., drug resistance, virulence factors, antibiogram).

The present invention is explained in greater detail in the figures herein and the description set forth below.

BRIEF DESCRIPTION OF THE FIGURES

FIG. 5 shows a bar graph of specific binding of PNA FISH probes to various *Candida* species.

DETAILED DESCRIPTION OF THE INVENTION

Figure 1:
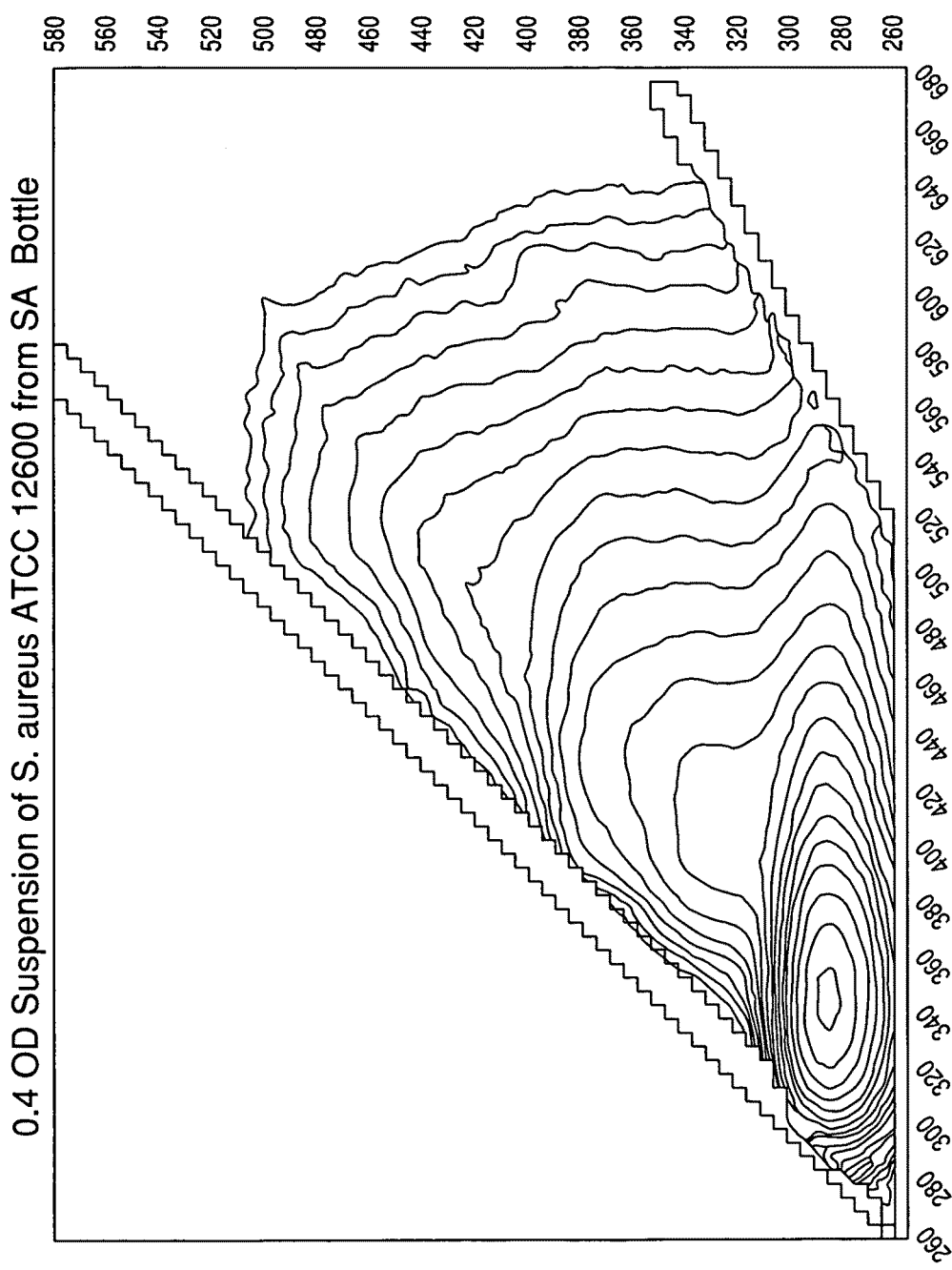
FIG. 1 shows an excitation-emission matrix for a suspension of *S. aureus*.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. Definitions.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "microorganism" is intended to encompass organisms that are generally unicellular, which can be multiplied and handled in the laboratory, including but not limited to, Gram-positive or Gram-negative bacteria, yeasts, molds, parasites, and mollicutes. Non-limiting examples of Gram-negative bacteria of this invention include bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia*, and *Legionella*. Non-limiting examples of Gram-positive bacteria of this invention include bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Corynebacteria*. Non-limiting examples of yeasts and molds of this invention include those of the following genera: *Candida, Cryptococcus, Nocardia, Penicillium, Alternaria, Rhodotorula, Aspergillus, Fusarium, Saccharomyces* and *Trichosporon*. Non-limiting examples of parasites of this invention include those of the following genera: *Trypanosoma, Babesia, Leishmania, Plasmodium, Wucheria, Brugia, Onchocerca*, and *Naegleria*. Non-limiting examples of mollicutes of this invention include those of the following genera: *Mycoplasma* and *Ureaplasma*.

As used herein, the term "identifier agent" is intended to encompass any compound that binds to or acts upon a microorganism to produce measurements that correlate with a known microorganism or microorganism group. The term "identifier agent" can also include any compound that is acted upon my the microorganism or a component thereof (e.g., an enzyme produced by said microorganism) and which can produce measurements that correlate with a known microorganism or microorganism group.

In one embodiment, as described in further detail herein, microorganisms from a sample or growth medium can be separated and interrogated to characterize and/or identify the microorganism present in the sample. As used herein, the term "separate" is intended to encompass any sample of microorganisms that has been removed, concentrated or otherwise set apart from its original state, or from a growth or culture medium. For example, in accordance with this invention, microorganisms may be separated away (e.g., as a separated sample) from non-microorganism or non-microorganism components that may otherwise interfere with characterization and/or identification. The term may include a layer of microorganisms sandwiched between two other layers, e.g., microorganisms collected on top of a high-density cushion after centrifugation, or a layer of microorganisms collected on a solid surface (e.g., a filter membrane). The term may also include a collection of microorganisms that has passed partially through a layer (e.g., a density cushion). As such, a separated microorganism sample may include any collection or layer of microorganisms and/or components thereof that is more concentrated than, or otherwise set apart from, the original sample, and can range from a closely packed dense clump of microorganisms to a diffuse layer of microorganisms. Microorganism components that can be comprised in a separated form or sample include, without limitation, pilli, flagella, fimbriae, and capsules in any combination. Non-microorganism components that are separated away from the microorganisms may include non-microorganism cells (e.g., blood cells and/or other tissue cells) and/or any components thereof.

In yet another embodiment, as described in further detail herein, microorganisms from a sample or growth medium can be isolated and interrogated to characterize and/or identify the microorganism present in the sample. As used herein, the term "isolated" is intended to encompass any sample of microorganisms that has been at least partially purified from its original state, or from a growth or culture medium, and any non-microorganisms or non-microorganism components contained therein. For example, in accordance with this invention, microorganisms may be isolated away (e.g., as an isolated sample) from non-microorganisms or non-microorganism components that may otherwise interfere with characterization and/or identification. Non-microorganism components that are separated away from the microorganisms may include non-microorganism cells (e.g., blood cells and/or other tissue cells) and/or any components thereof.

In yet another embodiment, as described in further detail herein, microorganisms from a sample or growth medium can be pelleted and interrogated to characterize and/or identify the microorganism present in the sample. As used herein, the term "pellet" is intended to encompass any sample of microorganisms that has been compressed or deposited into a mass of microorganisms. For example, microorganisms from a sample can be compressed or deposited into a mass at the bottom of a tube by centrifugation, or other known methods in the art. The term includes a collection of microorganisms (and/or components thereof) on the bottom and/or sides of a container following centrifugation. Microorganism components that can be comprised in a pellet include, without limitation, pilli, flagella, fimbriae, and capsules in any combination. In accordance with this invention, microorganisms may be pelleted away (e.g., as a substantially purified microorganism pellet) from non-microorganism or non-microorganism components that may otherwise interfere with characterization and/or identification. Non-microorganism components that are separated away from the microorganisms may include non-microorganism cells (e.g., blood cells and/or other tissue cells) and/or any components thereof.

As used herein, the term "density cushion" refers to a solution having a homogenous density throughout.

The present invention provides methods for isolating, characterizing and/or identifying microorganisms in a sample. Moreover, the method may be particularly useful for the separation, characterization and/or identification of microorganisms from complex samples such as blood-containing culture media. The rapid methods also allow for the characterization and/or identification of microorganisms more quickly than prior techniques, resulting in faster diagnoses (e.g., in a subject having or suspected of having septicemia) and characterization/identification of contaminated materials (e.g., foodstuffs and pharmaceuticals). The steps involved in the methods of the invention, from obtaining a sample to characterization/identification of microorganisms, can be carried out in a very short time frame to obtain clinically relevant actionable information. In certain embodiments, the methods of the invention can be carried out in less than about 120 minutes, e.g., in less than about 110, 100, 90, 80, 70, 60, 50, 40, 30, 20, 15, 10, 5, 4, 3, 2, or 1 minute. The tremendous rapidity of the methods of the invention represents an improvement over prior methods. The methods can be used to characterize and/or identify any microorganism as described herein. In one embodiment, the microorganism is a bacterium. In another embodiment, the microorganism is a yeast. In another embodiment, the microorganism is a mold. In a further embodiment, the microorganism is a parasite. In another embodiment, the microorganism is a mollicute. Additionally, the methods of the invention can be fully automated, thereby reducing the risk of handling infectious materials and/or contaminating the samples.

In one aspect, the present invention is directed to a method of characterizing and/or identifying a microorganism, comprising:
(a) obtaining a test sample known to contain or that may contain microorganisms;
(b) layering the test sample over a density cushion in a container;
(c) adding an identifier agent to said sample and/or said density cushion;
(d) centrifuging said container to separate microorganisms from other components of said test sample and forming a pellet of microorganisms;
(e) interrogating said pellet and/or said one or more identifier agents to produce measurements which identify the microorganisms; and
(f) characterizing and/or identifying the microorganisms in the pellet based on the produced measurements and/or the presence or absence of said identifier agent or a metabolized form of the identifier agent in the pellet.

In another aspect, the present invention is directed to a method of isolating and identifying a microorganism, comprising:
(a) obtaining a test sample known to contain or that may contain microorganisms;
(b) optionally lysing cells in said test sample to produce a lysed sample;
(c) separating microorganisms from other components of said lysed sample to form a pellet of microorganisms;
(d) interrogating the pellet to produce measurements which identify the microorganisms;
(e) identifying the microorganisms based on the produced measurements; and
(f) recovering at least a portion of the pellet to produce recovered microorganisms;
(g) conducting one or more further tests on said recovered microorganisms.

In another embodiment of the invention, the methods involve recovering the pellet of microorganisms formed during the separation step or a portion thereof from the separation container prior to interrogation of the microorganisms. For example, after formation of the pellet, the fluids can be aspirated way from the pellet and the pellet resuspended in a suitable medium (e.g., a medium in which the microorganisms are viable). The resuspended microorganisms can be removed from the separation container. The microorganisms can then be interrogated for characterization and/or identification, e.g., in the suspension or after they have been repelleted. In other embodiments, the resuspended microorganisms can be interrogated in the separation container, e.g., in the suspension or after they have been repelleted. In a further embodiment, microorganisms recovered from the pellet can be used directly for further interrogation (e.g., Raman Spectroscopy, mass spectrometry) without being resuspended.

Samples

Samples that may be tested (i.e., a test sample) by the methods of the invention include both clinical and non-clinical samples in which microorganism presence and/or growth is or may be suspected, as well as samples of materials that are routinely or occasionally tested for the presence of microorganisms. The amount of sample utilized may vary greatly due to the versatility and/or sensitivity of the method. Sample preparation can be carried out by any number of techniques known to those skilled in the art although one of the advantages of the present invention is that complex sample types, such as, e.g., blood, bodily fluids, and/or other opaque substances, may be tested directly utilizing the system with little or no extensive pretreatment. In one embodiment, the sample is taken from a culture. In another embodiment, the sample is taken from a microbiological culture (e.g., a blood culture). In another embodiment, the sample is suspected of, or known to, contain microorganisms therein.

Clinical samples that may be tested include any type of sample typically tested in clinical or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. In another embodiment, the clinical sample can be cultured, and a culture sample used.

The present invention finds use in research as well as veterinary and medical applications. Suitable subjects from which clinical samples can be obtained are generally mammalian subjects, but can be any animal. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects. Subjects from which samples can be obtained include, without limitation, mammals, birds, reptiles, amphibians, and fish.

Non-clinical samples that may be tested also include substances, encompassing, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. The method is also particularly well suited for real-time testing to monitor contamination levels, process control, quality control, and the like in industrial settings. In another embodiment, the non-clinical sample can be cultured, and a culture sample used.

In one embodiment of the invention, samples are obtained from a subject (e.g., a patient) having or suspected of having a microbial infection. In one embodiment, the subject has or is suspected of having septicemia, e.g., bacteremia or fungemia. The sample may be a blood sample directly from the subject. The sample may be from a blood culture grown from a sample of the patient's blood, e.g., a BacT/ALERT® blood culture. The blood culture sample may be from a positive blood culture, e.g., a blood culture that indicates the presence of a microorganism. In certain embodiments, the sample is taken from a positive blood culture within a short time after it turns positive, e.g., within about 6 hours, e.g., within about 5, 4, 3, or 2 hours, or within about 60 minutes, e.g., about 55, 50, 45, 40, 35, 30, 25, 20, 15, 10, 5, 4, 3, 2, or 1 minute. In one embodiment, the sample is taken from a culture in which the microorganisms are in log phase growth. In another embodiment, the sample is taken from a culture in which the microorganisms are in a stationary phase.

The present invention provides high sensitivity for the detection, characterization and/or identification of microorganisms. This enables detection, characterization and/or identification without first having to go through the steps of isolating microorganisms by growing them on a solid or semisolid medium, and sampling the colonies that grow. Thus, in one embodiment of the invention, the sample is not from a microbial (e.g., bacteria, yeast, or mold) colony grown on a solid or semisolid surface. Thus, in one embodiment of the invention, the sample is not from a microbial (e.g., bacteria, yeast, or mold) colony grown on a solid or semisolid surface.

The volume of the sample should be sufficiently large to produce an isolated sample of microorganisms or a pellet of microorganisms which can be interrogated after the separation/isolation step of the methods of the invention is carried out. Appropriate volumes will depend on the source of the sample and the anticipated level of microorganisms in the sample. For example, a positive blood culture will contain a higher level of microorganisms per volume than a drinking water sample to be tested for contamination, so a smaller volume of blood culture medium may be needed as compared to the drinking water sample. In general, the sample size can be less than about 50 ml, e.g., less than about 40, 30, 20, 15, 10, 5, 4, 3, or 2 ml. In certain embodiments, the sample size can be about 1 ml, e.g., about 0.75, 0.5, or 0.25 ml. In certain embodiments in which the separation is carried out on a microscale, the sample size can be less than about 200 µl, e.g., less than about 150, 100, 50, 25, 20, 15, 10, or 5 µl. In some embodiments (e.g., when the sample is expected to comprise a small number of microorganisms), the sample size can be about 100 ml or more, e.g., about 250, 500, 750, or 1000 ml or more.

Optional Lysis Step

In some embodiments, after obtaining a sample, the next step in the method of the present invention is to selectively lyse undesired cells that may be present in the sample, e.g., blood cells and/or tissue cells. Cells may be lysed to permit separation of microorganisms from other components of the sample. The separation of microorganisms from other components prevents interference during the interrogation step. If non-microorganism cells are not expected to be present in the sample or not expected to interfere with the interrogation step, the lysis step may not need to be carried out. In one embodiment, the cells to be lysed are non-microorganism cells that are present in the sample and no microorganism cells that may be present in the sample are lysed. However, in some embodiments, the selective lysing of specific classes of microorganisms may be desirable and thus can be carried out according to the methods described herein and as are well known in the art. For example, a class of undesired microorganisms can be selectively lysed, e.g., yeast are lysed while bacteria are not or vice versa. In another embodiment, the desired microorganisms are lysed in order to separate a particular subcellular component of the microorganisms, e.g., cell membranes or organelles. In one embodiment, all of the non-microbial cells are lysed. In other embodiments, a portion of the non-microbial cells are lysed, e.g., enough cells to prevent interference with the interrogation step. The lysing of cells may be carried out by any method known in the art to be effective to selectively lyse cells with or without lysing microorganisms, including, without limitation, addition of a lysis solution, sonication, osmotic shock, chemical treatment, and/or a combination thereof.

A lysis solution is one that is capable of lysing cells, e.g., non-microorganism cells (e.g., by solubilizing eukaryotic cell membranes) and/or microorganism cells. In one embodiment, the lysis solution can comprise one or more detergents, one or more enzymes, or a combination of one or more detergents and one or more enzymes, and can further include additional agents. In one embodiment, the detergent can be a non-denaturing lytic detergent, such as octylphenol ethoxylate (e.g., Triton® X-100 Triton® X-100-R, Triton® X-114), NP-40, Genapol® C-100, Genapol® X-100, (Octylphenoxy) polyethoxyethanol (e.g., Igepal® CA 630, Arlasolve™ 200, polyoxyethylene 10 oleoyl ether (e.g., Brij® 96/97), CHAPS, octyl β-D-glucopyranoside, saponin, and nonaethylene glycol monododecyl ether (C12E9, polidocenol). Optionally, denaturing lytic detergents can be included, such as sodium dodecyl sulfate, N-laurylsarcosine, sodium deoxycholate, bile salts, hexadecyltrimethylammonium bromide, SB3-10, SB3-12, amidosulfobetaine-14, and C7BzO. Optionally, solubilizers can also be included, such as polyoxyethylene (20) oleyl ether (e.g., Brij® 98), polyoxyethylene 20 cetyl ether (e.g., Brij® 58), polyoxyethylene (23) lauryl ether (e.g., Brij® 35), polyoxyethylenesorbitan monooleate (e.g., Tween® 80), polyoxyethylene sorbitol ester (e.g., Tween® 20), polyoxyalkylene ether (e.g., Pluronic® L64, Pluronic® P84), non-detergent sulfobetaines (NDSB 201), amphipols (PMAL-C8), and methyl-β-cyclodextrin. Typically, non-denaturing detergents and solubilizers are used at concentrations above their critical micelle concentration (CMC), while denaturing detergents may be added at concentrations below their CMC. For example, non-denaturing lytic detergents can be used at a concentration of about 0.010% to about 10%, e.g., about 0.015% to about 1.0%, e.g., about 0.05% to about 0.5%, e.g., about 0.10% to about 0.30% (final concentration after dilution with the sample). In another embodiment, polyoxyethylene detergent detergents may be preferred. The polyoxyethylene detergent can comprise the structure $C_{12-18}/E_{9-10}$, wherein C12-18 denotes a carbon chain length of from 12 to 18 carbon atoms and E9-10 denotes from 9 to 10 oxyethylene hydrophilic head groups. For example, the polyoxyethylene detergent can be selected from the group consisting of Brij® 97, Brij® 96V, Genapol® C-100, Genapol® X-100, nonaethylene glycol monododecyl ether (polidocanol), or a combination thereof.

Enzymes that can be used in lysis solutions include, without limitation, enzymes that digest nucleic acids and other membrane-fouling materials (e.g., proteinase XXIII, DNase, neuraminidase, polysaccharidase, Glucanex®, and Pectinex®). Other additives that can be used include, without limitation, reducing agents such as 2-mercaptoethanol (2-Me) or dithiothreitol (DTT) and stabilizing agents such as magnesium, pyruvate, and humectants. The lysis solution can be buffered at any pH that is suitable to lyse the desired cells, and will depend on multiple factors, including without limitation, the type of sample, the cells to be lysed, and the detergent used. In some embodiments, the pH can be in a range from about 2 to about 13, e.g., about 6 to about 13, e.g., about 8 to about 13, e.g., about 10 to about 13. Suitable pH buffers include any buffer capable of maintaining a pH in the desired range, e.g., about 0.05 M to about 1.0 M CAPS.

In one embodiment, the sample and the lysis solution are mixed and then incubated for a sufficient time for lysis and solubilization of cell membranes to occur, e.g., about 1, 2, 3, 4, 5, 10, 15, 20, 25, 30, 40, 50, or 60 seconds, or about 2, 3, 4, 5, 6, 7, 8, 9, 10, 15, or 20 minutes or longer, e.g., about 1 second to about 20 minutes, about 1 second to about 5 minutes, or about 1 second to about 2 minutes. The incubation time will depend on the strength of the lysis solution, e.g., the concentration of the detergent and/or enzymes. In general, milder lysis buffers will require more time and a greater dilution of the sample to fully solubilize non-microbial cells. The strength of the lysis solution can be selected based on the microorganisms known to be or suspected to be in the sample. For microorganisms that are more susceptible to lysis, a mild lysis solution can be used. The lysis can take place at a temperature of about 2° C. to about 45° C., e.g., about 15° C. to about 40° C., e.g., about 30° C. to about 40° C. In one embodiment, the lysis solution can be loaded into a syringe and the sample can then be aspirated into the syringe such that mixing and incubation occurs within the syringe. In one embodiment, the lysis solution can be loaded into a syringe and the sample can then be aspirated into the syringe such that mixing and incubation occurs within the syringe.

In some embodiments, the lysis conditions (e.g., the solution or the incubation time), as well as the separation and/or interrogation steps, can be sufficient to kill some or all of the microorganisms in the sample. The methods of the present invention are highly versatile and do not require that all microorganisms be alive for the isolation and identification to occur. In certain embodiments, some or all of the microorganisms may be dead, with death occurring before, during, and/or after the steps of the methods being carried out.

Separation Step

The next step in the method of the present invention (e.g., the step after the sample has been lysed, if a lysing step is performed) is a separation step. The separation step can be carried out to separate the microorganisms from other components of the sample (e.g., non-microorganisms or components thereof) and to concentrate the microorganisms into a pellet that can be interrogated for identification and characterization purposes. The separation does not have to be complete, i.e., it is not required that 100% separation occur. All that is required is that the separation of the microorganisms from other components of the sample be sufficient to permit interrogation of the microorganisms without substantial interference from the other components. For example, the separation can result in a microorganism pellet that is at least about 10, 20, 30, 40, 50, 60, 70, 80, 90, 95, 96, 97, 98, or 99% pure or higher.

In one embodiment, the separation is carried out by a centrifugation step in which the sample (e.g., a lysed sample) is placed on top of a density cushion in a separation container and the container centrifuged under conditions which allow the microorganisms to be isolated (e.g., the microorganisms can form a pellet at the bottom and/or sides of the container). In accordance with this embodiment, other components of the sample (e.g., non-microorganisms or components thereof that may be present in the sample medium) stay on top of the density cushion or within the top portion of the density cushion. In general, any known container may be used for the separation step. In one embodiment, the separation container is the separation device disclosed in related U.S. patent application, Ser. No. 12/589,969, entitled "Separation Device for Use in the Separation, Characterization and/or Identification of Microorganisms", filed Oct. 30, 2009, and which is incorporated herein by reference. This separation step isolates the microorganisms away from materials in the sample, such as medium, cell debris, and/or other components that might interfere with interrogation of the microorganisms (e.g., by intrinsic fluorescence). In one embodiment, the density cushion also serves to separate live microorganisms from dead microorganisms (which do not pass through the density cushion). In another embodiment the density cushion does not comprise a density gradient, either before or after the centrifugation. In other words, the separation container is not centrifuged for a sufficient amount of time and/or acceleration for the material making up the density cushion to form a density gradient.

The density of the cushion is selected such that the microorganisms in the sample pass through the cushion while other components of the sample (e.g., blood culture broth, cell debris) remain on top of the cushion or do not pass all of the way through the density cushion. The density cushion may also be selected to separate live microorganisms (which pass through the cushion) from dead microorganisms (which do not pass through the cushion). Suitable densities will depend on the material used in the density cushion and on the sample to be separated. In one embodiment, the density of the cushion is in the range of about 1.025 to about 1.120 g/ml, e.g., about 1.030 to about 1.070 g/ml, about 1.040 to about 1.060 g/ml or any range between about 1.025 to about 1.120 g/ml. In another embodiment, the density of the cushion is about 1.025, 1.030, 1.035, 1.040, 1.045, 1.050, 1.055, 1.060, 1.065, 1.070, 1.075, 1.080, 1.085, 1.090, 1.095, 1.100, 1.105, 1.110, 1.115, or 1.120 g/ml.

The material for the density cushion can be any material that has the appropriate density range for the methods of this invention. In one embodiment, the material is colloidal silica. The colloidal silica may be uncoated (e.g., Ludox® (W.R. Grace, CT)) or coated, e.g., with silane (e.g., PureSperm® (Nidacon Int'l, Sweden) or Isolate® (Irvine Scientific, Santa Ana, Calif.)) or polyvinylpyrrolidone (e.g., Percoll™, Percoll™ Plus (Sigma-Aldrich, St. Louis, Mo.)). In one embodiment, the colloidal silica exhibiting the least interference with spectroscopic interrogation is selected, e.g., the material with the lowest intrinsic fluorescence. The colloidal silica may be diluted in any suitable medium to form the proper density, e.g., balanced salt solutions, physiological saline, and/or 0.25 M sucrose. Suitable densities can be obtained with colloidal silica at a concentration of about 15% to about 80% v/v, e.g., about 20% to about 65% v/v. Another suitable material for density cushions is an iodinated contrast agent, e.g., iohexol (Omnipaque™ NycoPrep™, or Nycodenz®) and iodixanol (Visipaque™ or OptiPrep™). Suitable densities can be obtained with iohexol or iodixanol at a concentration of about 10% to about 25% w/v, e.g., about 14% to about 18% w/v, for blood culture samples. Sucrose can be used as a density cushion at a concentration of about 10% to about 30% w/v e.g., about 15% to about 20% w/v, for blood culture samples. Other suitable materials that can be used to prepare the density cushion include low viscosity, high density oils, such as microscope immersion oil (e.g., Type DF; Cargille Labs, New York), mineral oil (e.g., Drakeol® 5, Draketex 50, Peneteck®; Penreco Co., Pennsylvania), silicone oil (polydimethylsiloxane), fluorosilicone oil, silicone gel, metrizoate-Ficoll® (LymphoPrep™), e.g., at a concentration of about 75% to about 100% for blood culture samples, diatrizoate-dextran (PolymorphoPrep™), e.g., at a concentration of about 25% to about 50% for blood culture samples, carboxymethyl cellulose, hydroxypropylmethyl cellulose, polyethylene oxide (high molecular weight), polyoxyalkylene ether (e.g., Pluronic® F127, Pluronic® F68), mixtures of Pluronic® compounds, polyacrylic acid, cross-linked polyvinyl alcohol, cross-linked polyvinyl pyrrolidine, PEG methyl ether methacrylate, pectin, agarose, xanthan, gellan, Gellan Gum (e.g., Phytagel™), sorbitol, a sucrose and epichlorohydrin copolymer (Ficoll® (e.g., Ficoll® 400 at a concentration of about 10% to about 15% for blood culture samples)), glycerol, dextran (e.g., at a concentration of about 10% to about 15% for blood culture samples), glycogen, cesium chloride (e.g., at a concentration of about 15% to about 25% for blood culture samples), perfluorocarbon fluids (e.g., perfluoro-n-octane), hydrofluorocarbon fluids (e.g., Vertrel XF), and the like as are well known in the art. In one embodiment, the density cushion is selected from one or more of colloidal silica, iodixanol, iohexol, cesium chloride, metrizoate-Ficoll®, diatrizoate-dextran, sucrose, Ficoll® 400, and/or dextran in any combination. The density cushion can also be made up of a combination of materials, e.g., a combination of colloidal silica and oil. Certain combinations of the above compounds may be beneficial for the separation and reading steps of the present invention. For example, combinations of compounds with different UV-quenching properties, such as cesium chloride and Iohexol.

The volume/height of the density cushion should be sufficient to achieve separation of the microorganisms from other sample components. The volume will depend on the size and shape of the separation container. In general, a volume of about 0.1 to about 5 ml can be used, e.g., about 0.2 to about 1 ml, e.g., about 0.2 ml to about 0.5 ml. If the separation is performed on a microscale, the volume of the density cushion can be about 1 µl to about 100 µl, e.g., about 5 µl to about 50 µl. The volume of sample laid or layered on top of the density cushion should be sufficient to provide enough microorganisms to produce a pellet suitable for interrogation. In general, any volume that fits into the container can be used. For example, a volume of about 0.1 ml to about 5 ml can be used, e.g., about 0.2 ml to about 1 ml, e.g., about 0.2 ml to about 0.5 ml. If the separation is performed on a microscale, the volume of sample can be about 1 µl to about 100 µl, e.g., about 5 µl to about 50 µl. The available space in the container for sample will depend on the size and shape of the container. In some embodiments, an intermediate layer (liquid or solid) can be placed on top of the density cushion before the sample is laid or layered on top in order to prevent any mixing of the density cushion and the sample. In one embodiment, the intermediate layer can be polyethylene beads. In another embodiment, a small air bubble can be positioned between the density cushion and the sample to prevent mixing. In a further embodiment, the density cushion can be layered on top of a high density material (e.g., a perfluorocarbon fluid) such that the microorganisms pass through the density cushion during the separation and collect at the interface between the density cushion and the high density material.

In one embodiment of the invention, the separation container is centrifuged in a swing out rotor so that the microorganisms form a pellet directly on the bottom of the container. The container is centrifuged at a sufficient acceleration and for a sufficient time for the microorganisms to be separated (e.g., a pellet formed) from other components of the sample. The centrifugation acceleration can be about 1,000×g to about 20,000×g, e.g., about 2,500×g to about 15,000×g, e.g., about 7,500×g to about 12,500×g, etc. The centrifugation time can be about 30 seconds to about 30 minutes, e.g., about 1 minute to about 15 minutes, e.g., about 1 minute to about 5 minutes. The centrifugation can be carried out at a temperature of about 2° C. to about 45° C., e.g., about 15° C. to about 40° C., e.g., about 20° C. to about 30° C. In one embodiment, the separation container comprises a closure, and the closure is applied to the container to form a hermetic seal prior to centrifugation. The presence of a closure decreases the risks from handling microorganisms that are or may be infectious and/or hazardous, as well as the risk of contaminating the sample. One of the advantages of the methods of the invention is the ability to carry out any one or more of the steps of the methods (e.g., lysis, separation, interrogation, and/or identification) with the microorganisms in a sealed container (e.g., a hermetically sealed container). The present methods, involving the use of automated systems, avoid the health and safety risks associated with handling of highly virulent microorganisms, such as occurs with recovery of microorganisms from samples for direct testing. In one embodiment, the container is not centrifuged for a sufficient time and/or force for a density gradient to form within the density cushion. The present invention does not involve ultracentrifugation of samples, e.g., centrifugation at forces greater than about 100,000×g. Further, the present invention does not involve isopycnic (equilibrium) sedimentation or banding.

The separation container may be any container with sufficient volume to hold a density cushion and a sample. As noted herein, the separation device disclosed in related U.S. patent application, Ser. No. 12/589,969, entitled "Separation Device for Use in the Separation, Characterization and/or Identification of Microorganisms", filed Oct. 30, 2009, and which is incorporated herein by reference, may be used in the practice of this invention. In one embodiment, the container fits or can be fitted into a centrifuge rotor. The volume of the container can be about 0.1 ml to about 25 ml, e.g., about 1 ml to about 10 ml, e.g., about 2 ml to about 8 ml. If the separation is done on a microscale, the volume of the container can be about 2 µl to about 100 µl, e.g., about 5 µl to about 50 µl. In one embodiment, the container has a wide internal diameter in an upper portion to hold the sample and the majority of the density cushion, and a more narrow internal diameter in a lower portion where the pellet of microorganisms is collected. The narrow portion can have an internal diameter of about 0.04 to about 0.12 inches, e.g., about 0.06 to about 0.10 inches, e.g., about 0.08 inches. The wide portion can have an internal diameter of about 0.32 to about 0.40 inches, e.g., about 0.34 to about 0.38 inches, e.g., about 0.36 inches. For microscale separations, the internal diameters can be even smaller. For example, the internal diameter of the narrow portion can be about 0.001 to about 0.04 inches, e.g., about 0.002 to about 0.01 inches. A tapered internal diameter portion can connect the upper and lower portions. The tapered portion can have an angle of about 20 to about 70 degrees, e.g., about 30 to about 60 degrees. In one embodiment, the lower narrow portion is less than half of the total height of the container, e.g., less than about 40%, 30%, 20%, or 10% of the total height of the container. The container can have a closure device attached or may be threaded to accept a closure device (e.g., a cap) such that the container can be hermetically sealed during centrifugation. In certain embodiments, the container is designed such that the microorganism sample or pellet can be readily recovered, or otherwise obtained or removed from the container after separation, either manually or in an automated manner (so that technicians are not exposed to the container contents). For example, the container can comprise a removable portion or a break-away portion which contains the pellet and which can be separated from the rest of the container. In another embodiment, the container comprises means for access to the pellet after separation, such as one or more ports or permeable surfaces for insertion of a syringe or other sampling device or for drawing off the pellet. In one embodiment, the container can be a tube, e.g., a centrifuge tube. In another embodiment, the container can be a chip or a card. In one embodiment, the container is a stand alone container, i.e., a device for separating a single sample. In other embodiments, the container is part of a device that comprises two or more separation containers such that multiple samples can be separated at the same time. In one embodiment, the device comprises 2, 3, 4, 5, 6, 7, 8, 9, 10, 12, 15, 20, 25, 30, 36, 42, 48, 60, 72, 84, 96, or more separation containers.

The container can comprise an optical window through which the interrogation can occur. The optical window may be on the bottom, top, and/or sides of the container. The window can be composed of any material that is transparent to light (e.g., at least a portion of the near infrared (NIR; 700 nm-1400 nm), ultraviolet (UV; 190 nm-400 nm) and/or visible (VIS; 400 nm-700 nm) light spectrum. Examples of suitable materials include, without limitation, acrylic, methacrylate, quartz, fused silica, sapphire, and/or a cyclic olefin copolymer (COC). The window can also be comprised of any material that is a vibrational structure which is distinguishable from the spectra of the microorganism. Other discrimination techniques such as confocal Raman spectroscopy can be utilized to acquire the vibrational spectra of the microorganism while rejecting the spectra of the window material; this technique is well-known to those skilled in the art. An additional technique is Spatially Offset Raman Spectroscopy in which the excitation fiber is displaced along the window from the emission (Rayleigh and Raman spectra). This technique is also known to those skilled in the art as a means of discriminating between a window material and a quantity to be measured beneath the window. In one embodiment, the entire container is made of optical window material. In another embodiment, the container may be prepared (e.g., molded) from two or more separate parts, such as an optical UV-VIS-NIR transparent or Raman transparent component for the optical window and another material (e.g., a lower-cost standard molding plastic) to make up the rest of the container. In one embodiment, the optical window is thin enough to permit spectroscopic interrogation, which will depend on the material of the window. In another embodiment, the optical window is as thin as possible to reduce interference with spectroscopic interrogation. For example, the window can have a thickness of less than about 0.20 inches, e.g., less than about 0.15, 0.10, or 0.05 inches.

In another embodiment, the separation is carried out by a filtration step in which the sample (e.g., a lysed sample) is placed in a device fitted with a selective filter or filter set with pore sizes that retain the microorganisms. The retained microorganisms may be washed by gently passing a suitable buffer through the filter. The washed microorganisms may then be interrogated directly on the filter and/or recovered for interrogation by directly sampling the surface of the filter or by back-flushing the filter with suitable aqueous buffer.

Interrogation Step

Once the microorganisms have been separated, isolated and/or pelleted, the separated sample, isolated sample or pellet can be interrogated to identify and/or characterize the microorganisms in the sample or pellet. In one embodiment, the interrogation takes place in a non-invasive manner, that is, the pellet is interrogated while it remains in the separation container. In another embodiment, the separation container remains sealed throughout the interrogation. The ability to identify the microorganisms in a non-invasive manner, optionally coupled with keeping the container sealed throughout the separation and identification/characterization process and automating some or all of the procedure avoids the constant handling of contaminated and/or infectious samples and greatly increases the safety of the entire process. Furthermore, the ability to characterize and/or identify microorganisms by direct interrogation without further processing of the sample or pellet (e.g., resuspension, plating, and growth of colonies), greatly increases the speed with which identification/characterization can be made. In one embodiment, the sample or pellet is recovered and/or resuspended and optionally removed from the separation container prior to interrogation. In another embodiment, the sample or pellet is recovered and/or resuspended after in situ interrogation and further interrogation is then carried out. For example, techniques such as latex agglutination tests or automated phenotypic identification tests that can be applied to isolated microorganisms but not a pellet of microorganisms can be carried out on the recovered and/or resuspended microorganisms.

In some embodiments, the isolated sample or pellet can be interrogated spectroscopically. In one embodiment, optical spectroscopic methods can be used to analyze one or more intrinsic properties of the microorganisms, e.g., a property present within the microorganism in the absence of additional agents, such as stains, dyes, binding agents, etc. In other embodiments, the optical spectroscopic methods can be used to analyze one or more extrinsic properties of the microorganisms, e.g., a property that can only be detected with the aid of additional agents. The interrogation can be carried out using, for example, fluorescence spectroscopy, diffuse reflectance spectroscopy, infrared spectroscopy, terahertz spectroscopy, transmission and absorbance spectroscopy, Raman spectroscopy, including Surface Enhanced Raman Spectroscopy (SERS), Spatially Offset Raman spectroscopy (SORS), transmission Raman spectroscopy, and/or resonance Raman spectroscopy. To enhance Raman (SERS) and fluorescence signals, microorganisms could either be coated with gold and/or silver nanoparticles prior to centrifugation, and/or the inner optical surface could be pre-coated with metal colloids of particular size and shape (refs: Lakowicz, *Anal. Biochem.* 337:171 (2005) for fluorescence; Efrima et al., *J. Phys. Chem. B.* (*Letter*) 102:5947 (1998) for SERS). Further details useful for interrogation of microorganism samples and/or pellet using Raman spectroscopy are disclosed in co-assigned U.S. patent application, Ser. No. 12/589,976, entitled "Methods for Separation, Characterization and/or Identification of Microorganisms using Raman spectroscopy", filed Oct. 30, 2009, which is incorporated herein by reference. In another embodiment, the nanoparticles are present in the density cushion prior to centrifugation and associate with microorganisms as the microorganisms pass through the density cushion. In other embodiments, the microorganisms in the pellet can be interrogated using mass spectrometry techniques, such as MALDI-TOF mass spectrometry, desorption electrospray ionization (DESI) mass spectrometry, GC mass spectrometry, LC mass spectrometry, electrospray ionization (ESI) mass spectrometry and Selected Ion Flow Tube (SIFT) spectrometry. In one embodiment, the isolated sample or pellet is interrogated while it remains in the separation container. The container can be interrogated through an optical window in the container. The optical window may be on the bottom and/or any side or sides and/or on the top of the container. In one embodiment, the separation container fits into or can be fitted into a holder in a spectrometer in a suitable position for interrogation. The spectroscopic interrogation can be carried out by any technique known to those of skill in the art to be effective for detecting and/or identifying one or more intrinsic or extrinsic properties of microorganisms. For example, front face fluorescence (where the exciting and emitted light enters and leaves the same optical surface, and if the sample is generally optically thick, the excitation light penetrates a very short distance into the sample (see, e.g., Eisinger, J., and J. Flores, "Front-face fluorometry of liquid samples," *Anal. Biochem.* 94:15 (1983)) can be used for identification of microorganisms in pellets. Other forms of measurement, such as epifluorescence, reflectance, absorbance, and/or scatter measurements, can also be employed in the present invention. In another embodiment, as described herein, the isolated sample or pellet can be removed for interrogation (e.g., the isolated sample or pellet can be removed and prepared for interrogation by mass spectrometry, as is well known in the art). In still further embodiments, the isolated sample or pellet can be interrogated using more than one means. For example, the isolated sample or pellet can be interrogated using fluorescence spectroscopy and Raman spectroscopy. In accordance with this embodiment, these interrogation steps may be carried out sequentially or simultaneously.

The sample illumination source, or excitation source, may be selected from any number of suitable light sources as known to those skilled in the art. Any portion of the electromagnetic spectrum that produces usable data can be used. Light sources capable of emission in the ultraviolet, visible and/or near-infrared spectra, as well as other portions of the electromagnetic spectrum, can be utilized and are known to those skilled in the art. For example, light sources may be continuum lamps such as a deuterium or xenon arc lamp for generation of ultraviolet light and/or a tungsten halogen lamp for generation of visible/near-infrared excitation. These light sources provide a broad emission range and the spectral bandwidth for specific excitation wavelengths may be reduced using optical interference filters, prisms and/or optical gratings, as are well known in the art.

Alternatively, a plurality of narrowband light sources, such as light emitting diodes and/or lasers, may be spatially and/or temporally multiplexed to provide a multi-wavelength excitation source. For example, light emitting diodes are available from 240 nm to in excess of 900 nm and the sources have a spectral bandwidth of 20-40 nm (full width at half maximum). Lasers are available in discrete wavelengths from the ultraviolet to the near-infrared and can be employed using multiplexing methods well known to those skilled in the art.

The spectral selectivity of any of the light sources may be improved by using spectral discrimination means such as a scanning monochromator. Other methods of discrimination may be utilized, as known to those of skill in the art, such as an acousto-optic tunable filter, liquid crystal tunable filter, an array of optical interference filters, prism spectrograph, etc., and in any combination. A consideration in selecting the spectral discriminator takes into the account the range of tunability as well as the level of selectivity. By way of illustration, for example, a discriminator might utilize the wavelength range of 300-800 nm with a selectivity of 10 nm. These parameters generally determine the optimum technology necessary to achieve the tunability range as well as the selectivity.

Typically, the light source results in the excitation of the sample, followed by measurement of the emission of fluorescence of the sample at predetermined time points or continuously. Similarly, the reflected light from interaction of the excitation source with the sample may be measured to provide pertinent data for detection and/or characterization.

The emission from the sample may be measured by any suitable means of spectral discrimination, most preferably employing a spectrometer. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device (CCD) detector array. In one embodiment, a discriminator allows the observation of the fluorescence and/or scattering signal by a photodetection means (such as a photomultiplier tube, avalanche photodiode, CCD detector array, and/or electron multiplying charge coupled device (EMCCD) detector array).

The spectroscopic technique is used to obtain measurements that are preferably provided as Excitation-Emission Matrix (EEM) measurements. As used herein, EEM is defined as the luminescent spectral emission intensity of fluorescent substances as a function of both excitation and emission wavelength, and includes a full spectrum or a subset thereof, where a subset may contain a single or multiple excitation/emission pairs(s). Additionally, a cross section of the EEM with a fixed excitation wavelength may be used to show the emission spectra for a specific excitation wavelength, and a cross section of the EEM with a fixed emission wavelength may be used to show the excitation spectra for a sample. In one embodiment, multiple EEMs are measured at more than one specific excitation-emission wavelength pair, e.g., at least at 2, 3, 4, 5, 6, 7, 8, 9, 10, or more specific excitation-emission wavelength pairs.

In accordance with one embodiment of the invention, it has been found that a front-face fluorescence spectroscopy provides an advantage in measuring the fluorescence and/or reflectance properties of highly scattering and highly quenching samples. In one embodiment, the front-face method may be particularly useful. For example, front-face fluorescence may be particularly useful in highly absorbent samples because the excitation and emission beam does not need to travel through the bulk of the sample, and thus, may be less affected by the interfering components that may be contained therein (e.g., blood cells and microbiological culture media). The optical surface of the container may be illuminated at such an angle as to provide acceptable results as known to those skilled in the art, (e.g., Eisinger, J., and J. Flores, "Front-face fluorometry of liquid samples," *Anal. Biochem.* 94:15-21 (1983)). In one embodiment, the system is designed such that the spectroscopic system measures diffuse reflected light at a minimum of one fixed angle in addition to measuring emitted fluorescence at a minimum of one fixed angle.

According to the invention, control measurements are taken for known microorganisms, thus allowing for correlation of measured test data with characterization of the microorganisms of interest using various mathematical methods known to those skilled in the art. For example, the data from samples may be compared with the baseline or control measurements utilizing software systems known to one skilled in the art. More particularly, the data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA) and/or Support Vector Machine (SVM). These methods may be used to classify unknown microorganisms of interest into relevant groups based on existing nomenclature, and/or into naturally occurring groups based on the organism's metabolism, pathogenicity and/or virulence in designing the system for monitoring, detecting and/or characterizing the organism as described previously.

In another embodiment, the microorganisms in the pellet can be interrogated using mass spectrometry techniques. In accordance with this embodiment, the sample or pellet may be recovered and/or resuspended and optionally removed from the separation container prior to interrogation. In another embodiment, the sample or pellet is recovered and/or resuspended after in situ interrogation and further interrogation is then carried out. For example, techniques such as latex agglutination tests or automated phenotypic identification tests that can be applied to isolated microorganisms but not a pellet of microorganisms can be carried out on the recovered and/or resuspended microorganisms. After the sample has been resuspended, a portion of the sample can be removed from the suspension and placed onto a plate for introduction into a mass spectrometer. A highly absorptive substance is deposited on top of the sample (e.g. matrix); this material has a very high optical absorption coefficient with respect to the laser frequency that is used to ionize the sample (e.g. for a nitrogen laser the emission wavelength is 337 nm so the absorptive material would have a large absorption coefficient at a wavelength of 337 nm). After the sample and absorptive substance have dried, the plate is inserted into the mass spectrometer. After the time required to pump the sample down (i.e. remove atmospheric gases from the sample so that it is in an environment of 10-5 to 10-7 torr), the sample is introduced into the ionization chamber of the mass spectrometer. The sample is aligned with the system. When optimal alignment is achieved, the nitrogen laser is pulsed. The absorption of the laser energy by the matrix causes it to ablate from the plate's surface due to the high energy deposited. As a side effect, portions of the microorganism cell are also vaporized and ionized in the process. These ions are accelerated to a known kinetic energy by the generation of an electrostatic field between the plate and the entrance to the mass spectrometer's flight tube (i.e. this portion of the system is the mass/charge discriminator). All singly charged ions, regardless of mass, will have the same kinetic energy at the entrance to the flight tube, but they will have velocities that are inversely proportional to their masses. From there, ions move down the flight tube towards the detector, and lighter ions will arrive before heavier ions (the flight tube is the mass/charge discriminator). The detector generates an electrical charge every time an ion impacts the detector. The output of the detector is digitized and the output displays mass/charge ratio on one axis and number of impacts on the other axis.

In accordance with this embodiment, the separated microorganism sample can be interrogated by mass spectrometry to acquire a mass spectrum of said microorganism and characterizing and/or identifying the microorganism by comparison of the measured mass spectrum with reference mass spectra and/or with the known or predicted masses of cellular components of known microorganisms. Further detail useful for interrogation of microorganism samples and/or pellet are disclosed in co-assigned U.S. patent application, Ser. No. 12/589,936, entitled "Methods for Separation, Characterization and/or Identification of Microorganisms using Mass Spectrometry", filed Oct. 30, 2009, which is incorporated herein by reference.

In yet another embodiment, non-spectroscopic measurements from the detection system, such as detection times and growth rates can be used to assist in the characterization and/or identification of microorganisms from the isolated sample or pellet. Additionally, measurements taken from a photographic image of the lower region of the separation device can provide valuable information on the identity of the isolate, such as pellet size, shape, color and density.

In some embodiments of the invention, characterization and/or identification of the microorganisms in the isolated sample or pellet need not involve identification of an exact species. Characterization encompasses the broad categorization or classification of biological particles as well as the actual identification of a single species. Classification of microorganism from an isolated sample or pellet may comprise determination of phenotypic and/or morphologic characteristics for the microorganism. For example, characterization of the biological particles may be accomplished based on observable differences, such as, composition, shape, size, clustering and/or metabolism. In some embodiments, classification of the biological particles of interest may require no prior knowledge of the characteristics of a given biological particle but only requires consistent correlations with empiric measurements thus making this method more general and readily adaptable than methods based on specific binding events or metabolic reactions. As used herein "identification" means determining to which family, genus, species, and/or strain a previously unknown microorganism belongs to. For example, identifying a previously unknown microorganism to the family, genus, species, and/or strain level.

In some instances, characterization encompasses classification models which provide sufficient useful information for action to be taken. As used herein, the preferred classification models comprise grouping into one or more of the following: (1) Gram Groups; (2) Clinical Gram Groups; (3) Therapeutic Groups; (4) Functional Groups; and (5) Natural Intrinsic Fluorescence Groups.

(1) Gram Groups: Within the Gram Groups classification, microorganisms may be placed into one of three broad classification categories based on their Gram staining reaction and overall size, said groups selected from one or more of the following: (a) Gram positive microorganisms that stain dark blue with Gram staining; (b) Gram negative microorganisms that stain red with Gram staining; and (c) yeast cells that stain dark blue with Gram staining, but are very large rounded cells that are distinguished from bacteria by their morphological characteristics and size.

(2) Clinical Gram Groups: The Gram Groups may be further divided into several sub-categories representing distinguishing morphological features. These sub-categories comprise all the relevant clinical information reported by an experienced laboratory technologist, and thus provide a higher level of identification than a positive or negative Gram reaction. This particular classification is very helpful because it eliminates concerns about relying on the quality of a Gram stain and/or the skill level of the technician reading the smear by providing the equivalent clinically relevant information with an automated system. More specifically, subcategories of microorganisms based on this classification model may be selected from one or more of the following: (a) cocci, which are small rounded cells; (b) diplococci, which are two small rounded cells joined together; (c) rods, which are rectangular shape; and (d) bacilli, which are rod shaped. Examples of these sub-categories that can be ascertained by additional morphological information include: (i) Gram positive cocci; (ii) Gram positive cocci in chains; (iii) Gram positive cocci in clusters (i.e., "grape-like" clusters); (iv) Gram positive diplococci; (v) Gram positive rods; (vi) Gram positive rods with endospores; (vii) Gram negative rods; (viii) Gram negative coccobacilli; (ix) Gram negative diplococci; (x) yeast; and (xi) filamentous fungi.

(3) Therapeutic Groups: The therapeutic groups comprise multiple microbial species that, when isolated from particular specimen types, are treated with the same class of antibiotics or mixture of antibiotics (e.g., as described in "*Sanford Guide to Antimicrobial Therapy* 2008"). In many cases, identity to the species level is not required by the clinician to enable a change from initial empiric therapy to a more targeted therapy because more than one species can be treated with the same choice of antibiotic(s). This classification level correctly places these "same-treatment" microorganisms into single therapeutic categories. Examples of this characterization level include the ability to distinguish highly resistant *Enterobacteriacae* (*EB*) species from sensitive *EB* species (*Entero-*

*bacter* spp. from *E. coli*), or fluconazole-resistant *Candida* species (*C. glabrata* and *C. kruzei*) from sensitive *Candida* species (*C. albicans* and *C. parapsilosis*), and so on.

(4) Functional Groups: According to the invention, microorganisms may also be placed into several groups based upon a mixture of metabolic, virulence and/or phenotypic characteristics. Non-fermentative organisms may be clearly distinguished from fermentative ones. Furthermore, microorganism species that produce hemolysins may be grouped separately from non-hemolytic species. In some cases, these groups represent broader categories than genus level (e.g., coliforms, Gram negative non-fermentative rods), some at the genus level (e.g., *Enterococcus, Candida*), and some with closer to species-level discrimination (e.g., coagulase-negative staphylococci, alpha-hemolytic streptococci, beta-hemolytic streptococci, coagulase-positive staphylococci, i.e., *S. aureus*).

(5) Natural Intrinsic Fluorescence ("IF") Groups: Microorganisms may also be placed into categories based on their natural tendency to group together by their innate and/or intrinsic fluorescence characteristics. Some of these groups may be common to Therapeutic and Functional Group categories. These groupings may comprise individual species, such as *E. faecalis, S. pyogenes*, or *P. aeruginosa* that have characteristic IF signatures and/or may contain small groups of organisms with relatively conserved IF signatures such as the *K. pneumoniae-K. oxytoca* or *E. aerogenes-E. cloacae* groups.

In addition to measuring intrinsic properties of microorganisms (such as intrinsic fluorescence) for identification purposes, the methods of the present invention can further comprise the use of additional identifier agents to aid in the separation and/or identification process. Agents that bind to specific microorganisms, such as affinity ligands, can be used to separate microorganisms, to identify a class or species of microorganism (e.g., through binding to a unique surface protein or receptor) and/or to identify a characteristic of the microorganism (e.g., antibiotic resistance). Useful identifier agents include, without limitation, monoclonal and polyclonal antibodies and fragments thereof (e.g., anti-Eap for *S. aureus* identification), nucleic acid probes, antibiotics (e.g., penicillin, vancomycin, polymyxin B), aptamers, peptide mimetics, phage-derived binding proteins, lectins, host innate immunity biomarkers (acute phase proteins, LPS-binding protein, CD14, mannose binding lectin, Toll-like receptors), host defense peptides (e.g., defensins, cathelicidins, proteogrins, magainins), bacterocins (e.g., lantibiotics, such as nisin, mersacidin, epidermin, gallidermin, and plantaricin C, and class II peptides), bacteriophages, and dyes selective for nucleic acids, lipids, carbohydrates, polysaccharides, capsules/slime or proteins, or any combination thereof. If the agent does not itself give out a detectable signal, the agent can be labeled to provide a detectable signal, such as by conjugating the agent to a marker (e.g., visible or fluorescent). Markers include, without limitation, fluorescent, luminescent, phosphorescent, radioactive, Raman active and/or colorimetric compounds. The agent can be added to the microorganisms at any step in the methods of the invention, e.g., when the sample is obtained, during lysis, and/or during separation. In some embodiments, the presence of the agent in the pellet can be determined during interrogation of the pellet. Other useful identifier agents include substrates for microbial enzymes, chelating agents, photosensitizing agent, quenching agent, reducing agent, oxidizing agent, buffer, acid, base, solvent, fixative, detergents, surfactants, disinfectants (eg. alcohols, bleach, hydrogen peroxide) and toxic compounds (eg. sodium azide, potassium cyanide) and metabolic inhibitors such as cyclohexamide, etc. Similarly, many fluorescent compounds for measuring microbial cell viability, metabolism and/or membrane potential may be used as an identifier agent in the present invention. As would be readily appreciated by one of skill in the art, the sensitivity of a particular microorganism to any compound affecting its physical state or metabolism, such as an antibiotic, could be rapidly ascertained by adding the compound to the sample, lysis buffer, density cushion or any mixture thereof.

In one aspect of the invention, the method can further comprise a step of recovering the pellet of microorganisms and performing additional tests. In one embodiment, the pellet can be recovered by aspirating off the sample medium and density cushion. In another embodiment, the pellet can be recovered by inserting a syringe into the container and aspirating out the pellet while the sample medium and density cushion remain intact. The recovered pellet can then be resuspended in a suitable medium, e.g., saline. Once resuspended, the microorganisms can be subject to any further tests that are desired, as would be known to those of skill in the art and as described above. In particular, any test requiring clean samples of microorganisms can be carried out with the resuspended microorganisms. In some embodiments, additional identification tests can be performed. Examples of identification tests include Vitek® 2, amplified and non-amplified nucleic acid tests (NAT), chromogenic and latex agglutination assays, immunoassays, (e.g., employing labeled antibodies and/or other ligands), mass spectrometry (e.g., MALDI-TOF mass spectrometry) and/or other optical techniques such as infrared spectroscopy (FTIR) or Raman spectroscopy. Additional characterization tests can also be performed, such as resistance to antibiotics and/or other drugs. The additional characterization may be part of a test that was started during the initial separation and identification steps of the method. For example, the detection of methicillin resistant *S. aureus* can begin by adding labeled penicillin (e.g., fluorescent-, or Raman-labeled) to the sample prior to separation of the microorganisms. Once the pellet has been recovered and resuspended, the level of bound penicillin can be determined.

In one aspect of the invention, some or all of the method steps can be automated. Automating the steps of the methods allows a greater number of samples to be tested more efficiently and reduces the risks of human errors in handling samples that may contain harmful and/or infectious microorganisms. Of greater importance, however, automation can deliver critical results at any time of the day or night without delay. Several studies have shown that faster identification of the organisms causing sepsis correlates with improved patient care, shorter hospital stays and lower overall costs.

In one aspect of the invention, some or all of the method steps can be automated. Automating the steps of the methods not only allows more samples to be tested more quickly, it also reduces the risks of human errors in handling samples that may contain harmful and/or infectious microorganisms.

In certain embodiments of the invention, the methods can also be used to detect the presence of microorganisms in a test sample. In these embodiments, the methods comprise the steps of:

(a) obtaining a test sample;
(b) optionally lysing cells in said test sample to produce a lysed sample; and
(c) separating microorganisms from other components of said sample to form a pellet of microorganisms;

wherein the presence of a pellet indicates that microorganisms are present in the sample. In one embodiment, the pellet is detected with the naked eye. In other embodiments, the pellet is detected by interrogation, e.g., spectroscopically.

In some embodiments, the detection methods can be used to monitor samples for contamination by microorganisms, e.g., foodstuffs, pharmaceuticals, drinking water, etc. In one embodiment, the methods can be carried out in a repetitive fashion for constant monitoring for contamination, e.g., once a month, once a week, once a day, once an hour, or any other time pattern. In another embodiment, samples can be tested as needed, e.g., when contamination is suspected. In further embodiments, the detection methods can be used to look for the presence of microorganisms in clinical samples, e.g., blood cultures. For example, a sample can be removed from a blood culture at certain time points and the detection method carried out on the sample to determine if the blood culture is positive. In one embodiment, a sample may be taken at a set time point after inoculation of the culture, e.g., 24 hours after inoculation, to determine if the blood culture is positive. In another embodiment, samples can be taken from the blood culture regularly, e.g., every 12, 6, 4, or 2 hours or every 60, 50, 40, 30, 20, 15, 10, or 5 minutes, to identify positive blood cultures within a short time of being detectably positive. In certain embodiments of the detection methods, the detection step can optionally be followed by identification methods as described herein.

In one aspect of the invention, some or all of the method steps can be automated. Automating the steps of the methods allows a greater number of samples to be tested more efficiently and reduces the risks of human errors in handling samples that may contain harmful and/or infectious microorganisms. Of greater importance, however, automation can deliver critical results at any time of the day or night without delay. Several studies have shown that faster identification of the organisms causing sepsis correlates with improved patient care, shorter hospital stays and lower overall costs.

The present invention is further detailed in the following examples, which are offered by way of illustration and is not intended to limit the invention in any manner. Standard techniques well known in the art or the techniques specifically described below are utilized.

EXAMPLES

Example 1

Rapid Microbial Isolation and Identification Method

A suspension of colloidal silica (0.2-0.5 mL; 1.040-1.050 gm/mL density) was added to several conical microcentrifuge tubes. Lysed positive BacT/ALERT® SA blood culture broth samples (0.5-1.0 mL) were overlaid onto the colloidal silica suspension. Alternatively, the colloidal silica solution can be added underneath the lysed blood culture broth using a needle or canula. Positive broth from cultures containing the following microorganisms were tested:
  E. coli, ATCC 25922
  E. faecalis, ATCC 29212
  S. aureus, ATCC 12600
  P. aeruginosa, ATCC 10145

The tubes were capped, and then spun in a microcentrifuge for 2 min at about 10,000 g at room temperature (20-25° C.). The supernatants were aspirated, then the purified microbial pellets were resuspended in 0.45% w/v NaCl to an optical density @ 660 nm of 0.40.

Figure 2:
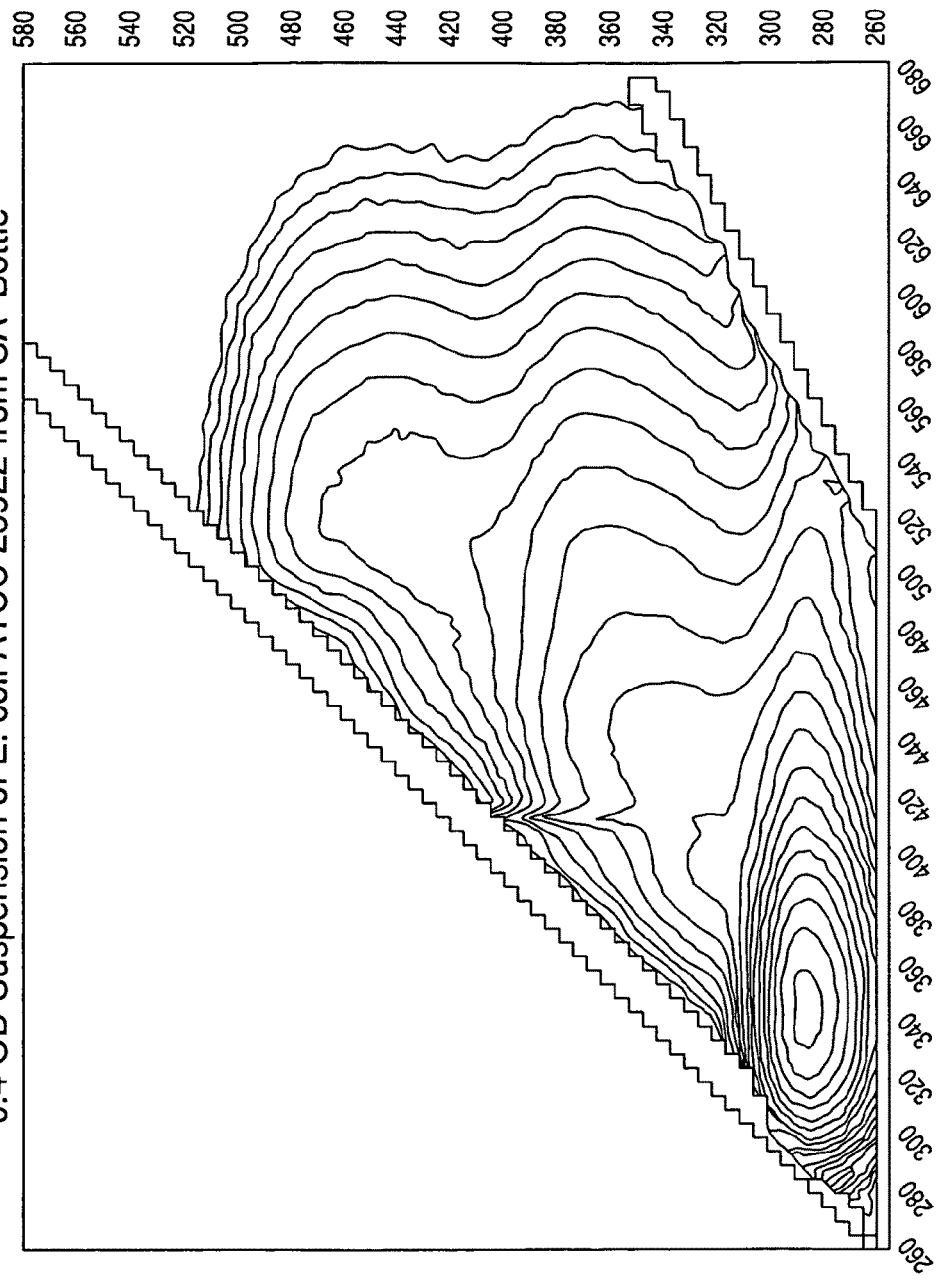
FIG. 2 shows an excitation-emission matrix for a suspension of *E. coli*.

One portion of each suspension was transferred to an acrylic cuvette and scanned in a spectrofluorimeter (Fluorolog® 3 (HORIBA Jobin Yvon Inc., New Jersey)) to measure microbial intrinsic fluorescence. Excitation-Emission Matrix spectra for S. aureus and E. coli are given in FIGS. 1 and 2.

A second portion was loaded into Vitek® 2 ID/AST cards (bioMérieux Inc., Missouri). The "direct" Vitek® 2 results were compared with those from suspensions of overnight grown colonies sub-cultured from the positive broth (traditional method). All 4 species gave excellent identification confidence levels with both the direct-from-blood culture and standard Vitek® methods, demonstrating that the density-based separation method provided microorganisms substantially free of blood and/or broth-derived particles and proteins.

Example 2

EDTA in Lysis Buffer as an Identifier Agent

Many lysis buffers, particularly those used for molecular methods, contain chelating agents such as EDTA to assist in the solubilization step. We assessed the impact of adding EDTA to the TX100-CAPS lysis buffer base using a panel of Gram-negative and Gram-positive microorganisms. Table 1 shows the rapid inhibitory effect of EDTA on P. aeruginosa and A. baumanii, but not on two other Gram-negative rods, B. cepacia and K. pneumoniae, or the Gram-positive S. aureus. Note that while EDTA was inhibitory to both P. aeruginosa and A. baumanii, the changes in major intrinsic fluorophores were very different between these two species. P. aeruginosa was the only organism tested that had a significant drop in both NADH and tryptophan fluorescence following EDTA treatment.

These experiments represents a good example of how certain additives or identifiers can be added to the lysis buffer to rapidly alter the base microbial intrinsic fluorescence profile of a particular microorganism and present opportunities for enhanced identification and further characterization of the isolate. As would be readily appreciated by one of skill in the art, the sensitivity of a particular microorganism to any compound affecting its physical state or metabolism could be rapidly ascertained by adding the compound to the sample, lysis buffer, density cushion or any mixture thereof. Similarly, alterations to the lysis conditions or the formulation of the selective lysis buffer (e.g. buffer pH, detergent type and its concentration) can produce characteristic changes in microbial intrinsic fluorescence.

TABLE 1

EDTA in Lysis Buffer as an Identifier Agent for P. aeruginosa

| No. | Microorganism | +20 mM EDTA | Tryptophan | NADH | Flavin | NADH/Flavin |
|---|---|---|---|---|---|---|
| 2 | P. aeruginosa | No | 2,266,444 | 4,483,691 | 62,491 | 72 |
| 2 | P. aeruginosa | Yes | 802,291 | 132,304 | 29,964 | 4 |
| 3 | A. baumanii | No | 1,274,164 | 2,157,065 | 47,163 | 46 |

TABLE 1-continued

EDTA in Lysis Buffer as an Identifier Agent for *P. aeruginosa*

| No. | Microorganism | +20 mM EDTA | Tryptophan | NADH | Flavin | NADH/Flavin |
|---|---|---|---|---|---|---|
| 4 | A. baumanii | Yes | 1,204,811 | 207,628 | 120,395 | 2 |
| 5 | B. cepacia | No | 2,199,711 | 2,577,516 | 42,135 | 61 |
| 6 | B. cepacia | Yes | 1,945,836 | 1,639,781 | 48,185 | 34 |
| 7 | K. pneumoniae | No | 2,770,779 | 2,691,451 | 151,112 | 18 |
| 8 | K. pneumoniae | Yes | 2,840,377 | 3,326,047 | 126,217 | 26 |
| 9 | S. aureus | No | 1,422,810 | 6,173,521 | 80,550 | 77 |
| 10 | S. aureus | Yes | 1,279,566 | 5,396,721 | 93,038 | 58 |

Example 3

Rapid In Situ Microbial Enzyme Assay

Several closely-related members of the Enterobacteraciae family can be differentiated by the presence or absence of an enzyme known as pyroglutamyl peptidase. For example, *E. aerogenes* is positive while *E. cloacae* is negative; *C. freundii* is positive and *E. coli* is negative.

Figure 3:
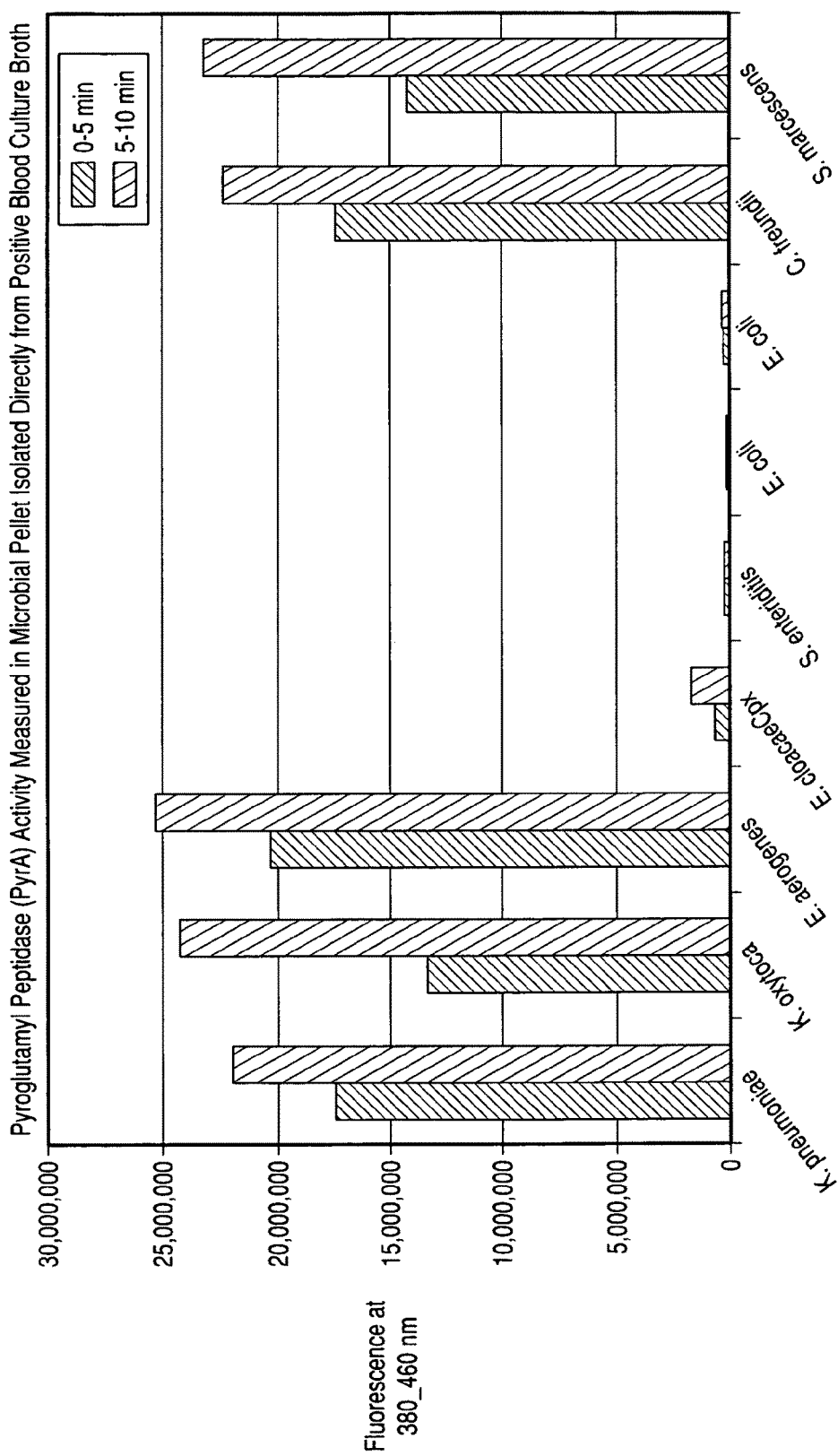
FIG. 3 shows a bar graph of pyroglutamyl peptidase (PyrA) activity measured in a microbial pellet isolated directly from a positive blood culture.
Figure 4:
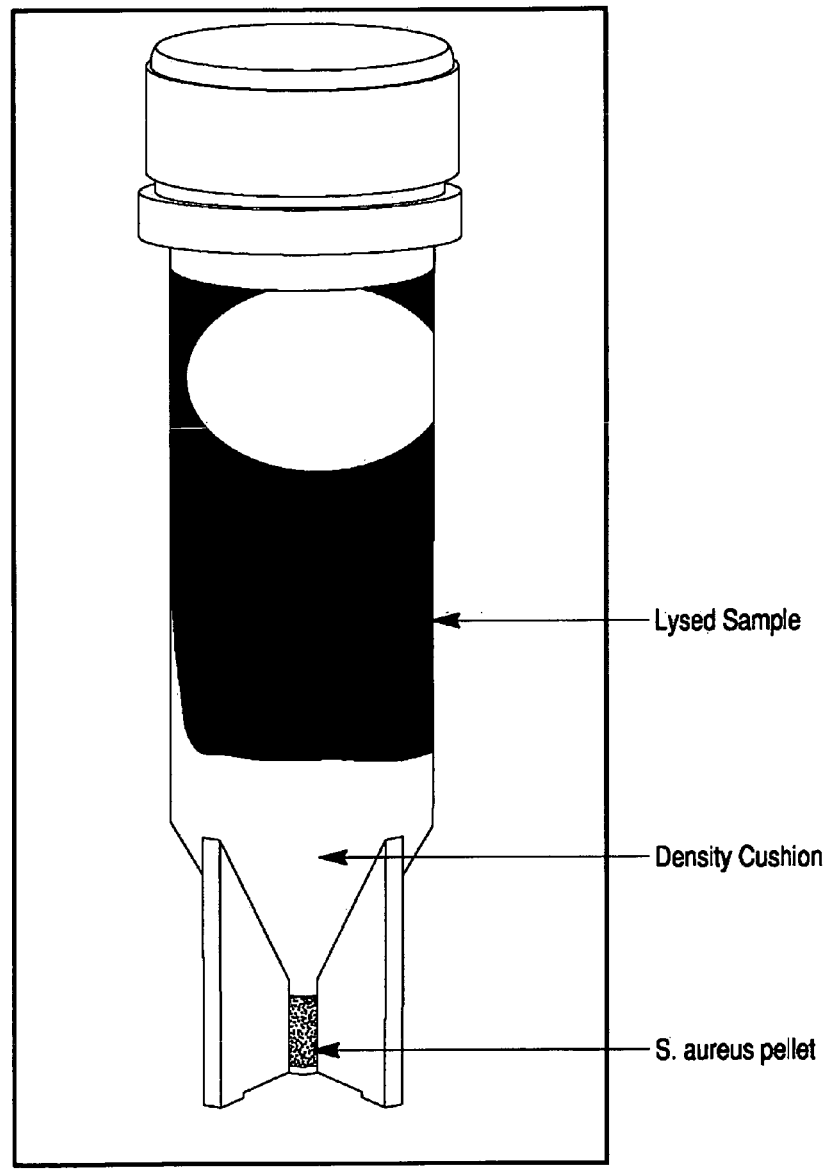
FIG. 4 is a photograph of a separation device showing a post-centrifugation of lysed microorganism-containing blood culture broth. Clearly visible in the photograph are the lysed blood culture, density cushion and microorganism pellet.

To test for microbial pyroglutamyl peptidase (PyrA), positive blood culture broth were treated as follows:

1. A 2.0 mL sample of positive broth was mixed with 1.0 mL of selective lysis buffer (0.45% w/v Brij® 97+0.3 M CAPS, pH 11.7), and then placed in a 37° C. water bath for 1 minute.
2. A 1.0 mL sample of lysate was overlayed onto 0.5 mL of density cushion (24% w/v cesium chloride+10 mM Hepes ph 7.4+0.005% Pluronic F-108) supplemented with 300 ug/mL L-pyroglutamic-acid-7AMC, contained in a custom-built optical separation tube. A polypropylene ball was present on the surface of the density cushion to facilitate loading without disturbing the two aqueous phases.
3. The optical separation tube was sealed with a screw-cap and centrifuged for 2 minutes at 10,000 rpm (Eppendorf® 5417R microcentrifuge fitted with a A-8-11 swing out rotor)(Eppendorf, New York)); see, e.g., FIG. 4, which shows a separation device post-centrifugation of lysed microorganism-containing blood culture broth.
4. The sealed tube was then transferred to a custom-built adapter which coupled the base of the tube directly to a 300 micron fiber optic probe connected to a spectrofluorimeter (Fluorolog® 3 (HORIBA Jobin Yvon Inc., New Jersey)).
5. The sedimented microbial pellet was read at the Ex/Em maximum for AMC (Ex 380 nm_Em 460 nm) immediately following centrifugation (represented by 0-5 min in FIG. 3) or after 5 minutes at 36° C. (5-10 min in FIG. 3).

The PyrA activity measured by this 5-10 minute assay was in full agreement with the Vitek® 2 GN Card Pyr A (bioMérieux Inc., Missouri) results for the same group of isolates. Turnover of this fluorogenic enzymatic substrate within a confined region of the optical separation tube by a large mass of metabolically-active cells was measureable within a few minutes. As would be readily appreciated by one of skill in the art, other microbial enzymatic activities may be measured in a similar manner.

Example 4

Rapid In Situ FISH Assay for Differentiation of *Candida* Species

A solution fluorescence in situ hybridization (FISH) assay was adapted to the method of the present invention using yeast colonies and a *C. albicans/C. glabrata* PNA FISH® kit (AdvanDx®, Massachusetts) as follows:

1. Using a disposable 1 µL loop, collect a loop full of yeast growth from Sabaraud-Dextraos Agar plates containing the following strains:
    a. *C. albicans*, StL # 304776
    b. *C. glabrata*, StL # 304749
    c. *C. tropicalis*, StL # 304421
2. Suspend the yeast growth directly into 50 µl, of a 1:1 mixture of Fixation reagent and Hybridization reagent from a *C. albicans/C. glabrata* PNA FISH® kit (AdvanDx®, Cat. No. KT006) in 1.5 mL microcentrifuge tubes
3. Vortex tubes briefly to mix yeast cells and reagents
4. Place tubes in a 55° C. waterbath for 30 minutes for hybridization to occur
5. Add 0.5 mL of the Wash Buffer, preheated to 55° C., to each tube.
6. Immediately, transfer the contents of each microcentrifuge tube to a optical separation tube prefilled with a 30% v/v of stock colloidal silica in 0.15 M NaCl (Isolate®; density=1.045 gm/mL)
7. Spin the separation tubes in an Eppendorf® 5417R microcentrifuge containing a A-8-11 swing out rotor for 2 minutes at 10,000 rpm.
8. Remove the tubes from the centrifuge. Transfer each tube to the custom-built 30-degree front face adapter for the Fluorolog® 3 spectrophotometer
9. Read the fluorescence of the yeast pellet in the bottom of each tube using a scan program including Ex500_Em530 (*C. albicans* probe), Ex560_Em590 (*C. glabrata* probe), cellular tryptophan, NADH and flavin regions
10. Export all data to Excel for analysis Under the assay conditions described above, the labeled RNA probes bound in higher quantities to their specific yeast species (FIG. 5). As would be readily appreciated by one of skill in the art, other microbe-specific RNA or DNA molecules may be measured using the in situ separation and read principle established in this invention.

That which is claimed is:

1. A method of characterizing and/or identifying a microorganism, comprising:
    (a) obtaining a test sample known to contain or that may contain microorganisms;
    (b) selectively lysing non-microorganism cells in said test sample to produce a lysed test sample;
    (c) layering said lysed test sample over a density cushion in a container;
    (d) adding an identifier agent to said lysed test sample and/or said density cushion;
    (e) centrifuging said container to separate microorganisms from other components of said test sample, said microorganisms passing through said density cushion and forming a pellet of microorganisms at the bottom of said container;

(f) interrogating said pellet using optical spectroscopy to produce measurements which identify the microorganisms, wherein said optical spectroscopy comprises intrinsic fluorescence; and (g) characterizing and/or identifying the microorganisms in the pellet based on the produced measurements.

2. The method of claim 1, wherein said identifier agent is selected from the group consisting of an affinity ligand, antibody or fragment thereof, an enzymatic substrate, nucleic acid probe, antibiotic, aptamer, peptide mimetic, phage-derived binding protein, lectin, host innate immunity protein, host defense peptide, bacterocin, bacteriophage, selective dye, chelating agent, photosensitizing agent, quenching agent, reducing agent, oxidizing agent, buffer, acid, base, solvent, alcohol, fixative, detergent, surfactant, disinfectant, toxic compound, metabolic inhibitor, oxidative metabolism probe, membrane potential protein, and any combination thereof.

3. The method of claim 1, wherein said identifier agent is a chelating agent.

4. The method of claim 1, wherein said identifier agent is a ethylenediametetraacetic acid (EDTA).

5. The method of claim 1, wherein said identifier agent is an enzymatic substrate.

6. The method of claim 1, wherein said identifier agent is an enzymatic substrate for pyroglutamyl peptidase.

7. The method of claim 1, wherein said identifier agent is a mixture of fluorescently labeled nucleic acid probes.

8. The method of claim 1, wherein steps (b)-(f) are carried out in a sealed container and wherein said interrogation step (f) is non-invasive.

9. The method of claim 1, wherein said interrogation step (f) further comprises removing said pellet from said container and subsequently interrogating said pellet using mass spectrometry.

10. The method of claim 9, wherein said optical spectroscopy further comprises fluorescence spectroscopy, diffuse reflectance spectroscopy, absorption and transmission spectroscopy, infrared spectroscopy, terahertz spectroscopy, Raman spectroscopy, surface enhanced Raman spectroscopy, spatially offset Raman spectroscopy, resonance Raman spectroscopy, or any combination thereof.

11. The method of claim 1, wherein said microorganisms are characterized based on one or more phenotypic and/or morphologic characteristics.

12. The method of claim 1, wherein said microorganisms are characterized into on one or more classification models selected from the group consisting of Gram Groups, Clinical Gram Groups, Therapeutic Groups, and Functional Groups.

13. The method of claim 1, wherein said microorganisms are identified to the genus level, species level, and/or strain level.

14. The method of claim 1, wherein said density cushion comprises one or more of colloidal silica, iodinated contrast agents, sucrose, microscope immersion oil, mineral oil, silicone oil, fluorosilicone oil, silicone gel, diatrizoate-dextran, carboxymethyl cellulose, hydroxypropylmethyl cellulose, polyethylene oxide (high molecular weight), polyoxyalkylene ether, polyacrylic acid, cross-linked polyvinyl alcohol, cross-linked polyvinyl pyrrolidine, PEG methyl ether methacrylate, pectin, agarose, xanthan, gellan, Gellan Gum, sorbitol, a sucrose and epichlorohydrin copolymer, glycerol, dextran, glycogen, cesium chloride, perfluorocarbon fluids, and/or hydrofluorocarbon fluid.

15. The method of claim 1, wherein said test sample is a culture sample known to contain microorganisms.

* * * * *